US009176142B2

(12) United States Patent
Yin et al.

(10) Patent No.: US 9,176,142 B2
(45) **Date of Patent: *Nov. 3, 2015**

(54) POLYMER CONJUGATE ENHANCED BIOASSAYS

(71) Applicant: ANP Technologies, Inc., Newark, DE (US)

(72) Inventors: Ray Yin, Newark, DE (US); Dujie Qin, Wilmington, DE (US); Jing Pan, Newark, DE (US)

(73) Assignee: ANP Technologies, Inc., Newark, DE (US)

( * ) Notice: Subject to any disclaimer, the term of this patent is extended or adjusted under 35 U.S.C. 154(b) by 178 days.

This patent is subject to a terminal disclaimer.

(21) Appl. No.: 14/059,387

(22) Filed: Oct. 21, 2013

(65) Prior Publication Data

US 2014/0045727 A1 Feb. 13, 2014

Related U.S. Application Data

(63) Continuation of application No. 11/913,265, filed as application No. PCT/US2006/016580 on May 2, 2006, now Pat. No. 8,563,329.

(60) Provisional application No. 60/677,218, filed on May 2, 2005.

(51) Int. Cl.

| | |
|---|---|
| ***G01N 33/545*** | (2006.01) |
| ***G01N 33/68*** | (2006.01) |
| ***B82Y 5/00*** | (2011.01) |
| ***B82Y 10/00*** | (2011.01) |
| ***G01N 33/532*** | (2006.01) |
| ***G01N 33/543*** | (2006.01) |

(52) U.S. Cl.

CPC .............. *G01N 33/6854* (2013.01); *B82Y 5/00* (2013.01); *B82Y 10/00* (2013.01); *G01N 33/532* (2013.01); *G01N 33/54353* (2013.01)

(58) Field of Classification Search

None

See application file for complete search history.

(56) References Cited

U.S. PATENT DOCUMENTS

| | | | |
|---|---|---|---|
| 4,289,872 | A | 9/1981 | Denkewalter et al. |
| 4,507,466 | A | 3/1985 | Tomalia et al. |
| 4,558,120 | A | 12/1985 | Tomalia et al. |
| 4,568,737 | A | 2/1986 | Tomalia et al. |
| 4,587,329 | A | 5/1986 | Tomalia et al. |
| 4,599,400 | A | 7/1986 | Tomalia et al. |
| 4,631,337 | A | 12/1986 | Tomalia et al. |
| 4,690,985 | A | 9/1987 | Tomalia et al. |
| 4,694,064 | A | 9/1987 | Tomalia et al. |
| 4,713,975 | A | 12/1987 | Tomalia et al. |

(Continued)

FOREIGN PATENT DOCUMENTS

| | | |
|---|---|---|
| WO | 9943287 | 9/1999 |
| WO | 9964863 | 12/1999 |

(Continued)

OTHER PUBLICATIONS

Maggio, "Enzyme-Immunoassay", 1980, p. 173.*

(Continued)

*Primary Examiner* — Chris L Chin

(74) *Attorney, Agent, or Firm* — MDIP LLC

(57) ABSTRACT

Incorporation of modified branched polymers in one or more components of assays enhances sensitivity, specificity or both, providing powerful point of use tests.

20 Claims, 18 Drawing Sheets

(56) References Cited

U.S. PATENT DOCUMENTS

| | | | |
|---|---|---|---|
| 4,737,550 | A | 4/1988 | Tomalia |
| 4,857,599 | A | 8/1989 | Tomalia et al. |
| 5,338,532 | A | 8/1994 | Tomalia et al. |
| 5,393,795 | A | 2/1995 | Hedstrand et al. |
| 5,393,797 | A | 2/1995 | Hedstrand et al. |
| 5,527,524 | A | 6/1996 | Tomalia et al. |
| 5,631,329 | A | 5/1997 | Yin et al. |
| 5,714,166 | A | 2/1998 | Tomalia et al. |
| 5,731,095 | A | 3/1998 | Milco et al. |
| 5,773,527 | A | 6/1998 | Tomalia et al. |
| 5,861,319 | A | 1/1999 | Lin et al. |
| 5,898,005 | A | 4/1999 | Singh et al. |
| 5,919,442 | A | 7/1999 | Yin et al. |
| 6,020,457 | A | 2/2000 | Klimash et al. |
| 6,043,336 | A | 3/2000 | Miller et al. |
| 6,083,708 | A | 7/2000 | Singh et al. |
| 6,121,056 | A | 9/2000 | Moll et al. |
| 6,274,713 | B1 | 8/2001 | Sieving et al. |
| 6,458,387 | B1 | 10/2002 | Scott et al. |
| 6,632,889 | B1 | 10/2003 | Yin et al. |
| 6,645,986 | B2 | 11/2003 | Walinsky et al. |
| 6,716,450 | B1 | 4/2004 | Yin et al. |
| 6,743,581 | B1 | 6/2004 | Vo-Dinh |
| 6,773,928 | B1 | 8/2004 | Yin et al. |
| 7,138,430 | B2 | 11/2006 | Garvey et al. |
| 7,338,651 | B2 | 3/2008 | Bornhop et al. |
| 7,384,976 | B2 | 6/2008 | Garvey et al. |
| 7,754,884 | B2 | 7/2010 | Bornhop et al. |
| 7,829,275 | B2 | 11/2010 | Franzen et al. |
| 8,188,116 | B2 | 5/2012 | Bornhop et al. |
| 8,323,621 | B2 | 12/2012 | Bornhop et al. |
| 8,372,868 | B2 | 2/2013 | Bornhop et al. |
| 8,563,329 | B2 * | 10/2013 | Yin et al. ...................... 436/518 |
| 2001/0055766 | A1 | 12/2001 | Aristarkhov et al. |
| 2002/0006622 | A1 | 1/2002 | Bradley et al. |
| 2002/0051981 | A1 | 5/2002 | Getts et al. |
| 2003/0026764 | A1 | 2/2003 | Griffiths |
| 2003/0059474 | A1 | 3/2003 | Scott et al. |
| 2003/0119208 | A1 | 6/2003 | Yoon et al. |
| 2003/0143596 | A1 | 7/2003 | Bentley et al. |
| 2003/0148379 | A1 | 8/2003 | Roitman et al. |
| 2003/0203915 | A1 | 10/2003 | Fang et al. |
| 2004/0023248 | A1 | 2/2004 | O'Malley et al. |
| 2005/0014174 | A1 | 1/2005 | Burmeister et al. |
| 2005/0277145 | A1 | 12/2005 | Haines et al. |
| 2006/0041058 | A1 | 2/2006 | Yin et al. |
| 2008/0114077 | A1 | 5/2008 | Yin et al. |

FOREIGN PATENT DOCUMENTS

| | | |
|---|---|---|
| WO | 0043044 | 7/2000 |
| WO | 0152979 | 7/2001 |

OTHER PUBLICATIONS

Benters et al., “Dendrimer . . . microarrays,” ChemBioChem 2, 686-694, 2001.

Singh, “Terminal Groups . . . Proteins,” Bioconj Chem 9, 54-63, 1998.

Fischer-Durand et al., “Synthesis . . . immunoassay,” ChemBioChem 5, 519-525, 2004.

Ong et al., “Dendrimer . . . detection,” Anal Chim Acta 444, 143-148, 2001.

Diamandis et al., “The Biotin . . . Biotechnology,” Clin. Chem. 37/5:625-636, 1991.

* cited by examiner

Polypropyleneimine Dendrimer-4

Polypropyleneimine Dendrimer-8

Polypropyleneimine Dendrimer-8, 16, 32, 64, or 128

PAMAM Modified Polypropyleneimine Dendrimer-8, 16, 32, 64, or 128 a) Adsorbent pad, b) biotinylated Ab, either on a separate pad or on the adsorbent pad, c) Streptavidin-gold conjugate, d-g) capture Abs for different targets, h) control Ab, i) liquid receiving pad.

a) Adsorbent pad, b) Streptavidin-gold conjugate, either on a separate pad or on the adsorbent pad, c) biotinylated Ab, d-g) capture Abs for different targets, h) control Ab, i) liquid receiving pad.

a) Adsorbent pad, b) Streptavidin-gold conjugate, either on a separate pad or on the adsorbent pad, c) biotinylated Ab, (b and c are on top of each other), d-g) capture Abs for different targets, h) control Ab, i) liquid receiving pad.

a) Adsorbent pad, b) biotinylated Ab, either on a separate pad or on the adsorbent pad, c) Streptavidin-gold conjugate, (b and c are on top of each other), d-g) capture Abs for different targets, h) control Ab, i) liquid receiving pad.

a) Adsorbent pad, b) biotinylated Ab, c) Streptavidin-gold conjugate, (a, b, c are on the same pad), d-g) capture Abs for different targets, h) control Ab, i) liquid receiving pad.

a) Adsorbent pad, b) Streptavidin-gold conjugate, c) biotinylated Ab, (a, b, c are on the same pad), d-g) capture Abs for different targets, h) control Ab, i) liquid receiving pad.

a) Adsorbent pad, b) biotinylated Ab, c) Streptavidin-gold conjugate, d-g) capture Abs for different targets, h) control Ab, i) liquid receiving pad. A-h) are on the same membrane.

a) Adsorbent pad, b) Streptavidin-gold conjugate, c) biotinylated Ab, d-g) capture Abs for different targets, h) control Ab, i) liquid receiving pad. A-h) are on the same membrane.

1. Detection of Ricin toxoid @ 200 ng/mL using non-polymer-Ab based assays
2. Detection of Ricin toxoid @ 20 ug/mL using non-polymer based assays
3. Detection of Ricin toxoid @ 20 ng/mL using polymer based assays 1. Direct detection of gold labeled IgG using non-polymer based assays
2. Direct detection of gold labeled IgG using polymer based assays 1. MSBP-FIG8C
2. MSBP-FIG8A
3. MABP-FIG8B
4. MABP-FIG8C
5. MABP-FIG8D
6. MABP-FIG8A
7. MABP
8. MSBP

POLYMER CONJUGATE ENHANCED BIOASSAYS

FIELD OF THE INVENTION

The present invention concerns the use of branched polymers (BP) in composite materials, such as conjugates, which can be employed, for example, in assay applications related to use in agriculture, environmental studies, diagnostics, drug monitoring, drug target screening, lead optimization, therapeutics and so on.

BACKGROUND OF THE INVENTION

In recent years, a new class of polymers called dendritic polymers, including both Starburst dendrimers (or Dense Star polymers) and Combburst dendrigrafts (or hyper comb-branched polymers), have been developed and extensively studied in industrial and academic laboratories. These polymers often exhibit: (a) a well-defined core molecule, (b) at least two concentric dendritie layers (generations) with symmetrical (equal) branch junctures, and (c) exterior surface groups, as described in Tomalia's U.S. Pat. Nos. 4,435,548; 4,507,466; 4,568,737; 4,587,329; 5,338,532; 5,527,524; and 5,714,166. Examples include polyethyleneimine dendrimers such as those disclosed in U.S. Pat. No. 4,631,337; polypropyleneimine dendrimers such as those disclosed in U.S. Pat. Nos. 5,530,092; 5,610,268; and 5,698,662; Frechet-type polyether and polyester dendrimers, core-shell tecto-dendrimers, and others as described in "Dendritic Molecules", edited by G R Newkorne et al., VCH Weinheim, 1996, and "Dendrimers and Other Dendritic Polymers", edited by J M J Frechet and D A Tomalia, John Wiley & Sons, Ltd., 2001.

Similar to dendrimers, Combburst dendrigrafts are also constructed with a core molecule and concentric layers with symmetrical branches through a stepwise synthetic method. In contrast to dendrimers, Combburst dendrigrafts or polymers are generated with monodisperse linear polymeric building blocks (Tonialia's U.S. Pat. No. 5,773,527 and Yin's U.S. Pat. Nos. 5,631,329 and 5,919,442). Moreover, the branch pattern is also very different from that of dendrimers. For example, Combburst dendrigrafts form branch junctures along the polymeric backbones (chain branches), while Starburst dendrimers often branch at the termini (terminal branches). Due to the utilization of living polymerization techniques, the molecular weight distributions (Mw/Mn) of these polymeric building blocks (core and branches) are often very narrow. As a result, Combburst dendrigrafts, produced through a graft-upon-graft process, are rather well defined with molecular weight distributions (Mw/Mn) often less than 1.2.

Dendrimers and dendrigrafts have been shown to possess unique carrier properties for bioactive molecules, as described in Tomalia's U.S. Pat. Nos. 5,338,532; 5,527,524; and 5,714,166 for Dense Star Polymers, and Yin's U.S. Pat. No. 5,919,442 for Hyper Comb-Branched Polymers. These unique properties (i.e., surface functional groups and interior void spaces) have been primarily attributed to the well-controlled, symmetrical dendritic architecture with predictable branching patterns (either symmetrical termini or polymeric chain branching) and molecular weights.

Other symmetrically branched polymers (SBP) could include symmetrical star- or comb-shaped polymers such as symmetrical star or comb-shaped polyethyleneoxide, polyethyleneglycal, polyethyleneimine, polypropyleneimine, polymethyloxazoline, polyethyloxazoline, polystyrene, polymethylmethacrylate, polydimethylsiloxane, and/or a combination thereof.

So far, none of the existing prior art has utilized modified symmetrically branched polymers for target recognition purposes, particularly for assay and microarray related applications, wherein transporting, anchoring, and orienting biologically active materials from a solution onto a solid surface are required.

These symmetrically branched dendrimers are different from asymmetrically branched (ABP) dendrimers (Denkewalter's U.S. Pat. Nos. 4,289,872; 4,360,646; and 4,410,688). The latter possess asymmetrical (unequal) branch junctures.

A random ABP (ran-ABP) possesses: a) no core, b) functional groups both at the exterior and in the interior, c) variable branch lengths and patterns (i.e., termini and chain branches), and d) unevenly distributed interior void spaces. Although a regular ABP (reg-ABP) possesses a core, the functional groups are both at the exterior and in the interior. Therefore, both ran-ABP and reg-ABP are generally considered to be unsuitable for carrying bioactive molecules.

The preparation of reg-ABP made of polylysine has been described, as illustrated in U.S. Pat. Nos. 4,289,872; 4,360,646; and 4,410,688.

The synthesis and mechanisms of ran-ABPs, such as made of polyethyleneimine (PEI), have been studied (see G D Jones et al., J. Org. Chem. 9, 125 (1944), G D Jones et al., J. Org, Chem. 30, 1994 (1965), and CR Dick et al., J. Macromol. Sci, Chem., A4 (6), 1301-1314, (1970)). Ran-ABP, such as made of polyoxazoline, i.e., poly(2-methyloxazoline) and/or poly (2-ethyloxazoline), have been studied by Litt (J. Macromol. Sci. Chem. A9(5), pp. 703-727 (1975)) and Warakornski (J. Polym. Sci. Polym. Chem. 28, 3551 (1990)).

Most of the prior art involved the utilization of polyethyleneimine polymers as coating materials to alter the characteristics of solid surfaces (i.e. changing charges, charge densities and hydrophobicity). The coating aspects of polyethyleneimine polymers have been described in J Ness's U.S. Pat. No. 6,150,103 and K Moynihan's U.S. Pat. No. 6,365,349. Polyethylmeimines have also been tested as to carrying DNA molecules for gene transfection studies. However, the polymers were found to be cytotoxic.

Randomly branched poly(2-ethyloxazoline) has also been utilized to physically encapsulate protein molecules (U.S. Pat. No. 6,716,450). However, such an approach was not designed for the direct, covalent linking of ABP with bioactive materials for bioassay applications.

So far, none of the existing prior art has utilized modified ran-ABP and reg-ABP for target recognition purposes, particularly for assay and microarray related applications, wherein transporting, anchoring, and orienting biologically active materials from a solution onto a solid surface is required.

Such dendrimers can be produced by repetitive protecting and deprotecting procedures through either a divergent or a convergent synthetic approach. Since both symmetric and asymmetric dendrimers utilize small molecules as molecular building blocks for the cores and the branches, the molecular weights of these dendrimers are often precisely defined. In the case of lower generations, a single molecular weight dendrimer is often obtained.

Since the completion of the human genome project, more and more researchers have realized that the elucidation of biological pathways and mechanisms at the protein level is actually far more important than at the genetic level. This is because the former is more closely related to different diseases and disease stages. With this strong demand push, a new forum called proteomics has recently become a major research focus for both industrial and academic researchers.

Currently, three major research tools have been employed in the proteomics research arena, primarily for the discovery, high throughput screening, and validation of new protein targets and drug leads. These tools include two dimensional (2-D) gel electrophoresis, mass spectrometry, and more recently, protein microarrays. In contrast to the lengthy 2-D gel procedures and tedious sample preparation (primarily separations) involved in mass spectrometry analysis, protein microarrays provide a fast, easy, and low-cost method to screen large numbers of proteins, as well as their functions. Therefore, microarrays are highly desired by proteomics researchers.

However, the protein-based microarray technology is far less developed than gene microarrays. The construction of a protein/antibody chip presents daunting challenges not encountered in the development of classical immunoassays or of DNA chips. In general, proteins are more sensitive to their environment than nucleic acids. The hydrophobicity of many membrane, glass, and plastic surfaces can cause protein denaturation, rendering the capture molecules inactive and resulting in lower sensitivity and higher noise-to-signal ratios. In other words, to construct a protein microarray, one must be able to overcome at least three major problems, protein denaturation, immobilization, and orientation.

For example, a protein molecule often folds into a three-dimensional structure in solution for and to maintain biological activity. On interaction with different solid surfaces, for example, during immobilization of proteins onto membranes, glass slides, or micro/nanoparticles, the three-dimensional structure of the protein molecule often collapses, thus losing biological activity. In addition, proteins often do not have the ability to adhere onto different surfaces.

To immobilize the protein molecule on a surface, a direct covalent linking reaction or an electrostatic interaction (physical adsorption) often has to be employed. Heterogeneous chemical reactions often are incomplete, yielding undesired side products (i.e. incomplete modification of surfaces), and in some cases, also partially denatured proteins during different reaction stages.

The electrostatic interaction relies heavily on the isoelectric point of the proteins, as well as the pH of the buffer solutions. While pH is manipulable, the efficacy of reaction of some proteins is low.

Both approaches tend to give irreproducible results due to the complexity involved in these procedures. The lot-to-lot reproducibility is, therefore, very poor. As a result, there is a great interest in modifying solid substrates, but not the protein molecule itself. A variety of polymers, including polyethyleneimine polymers, have been utilized as coating materials to alter the characteristics of solid surfaces for the construction of protein arrays, as described in U.S. Pat. Nos. 6,406,921 and 6,773,928.

So far, none of the prior art approaches utilizes modified branched polymers as carriers for bioactive materials, particularly for the construction of assays and microarrays.

SUMMARY OF THE INVENTION

In one aspect, the present invention is directed to polymer labeling conjugate materials comprising modified branched polymers (MBP) associated with desired materials, processes for preparing these polymers and conjugates, compositions containing the conjugates, and methods of using the conjugates and compositions. Branched polymers include symmetrical and asymmetrical polymers, random or regular.

Also included is a modified branched polymer associated with multiple units of carried material, and each with the same or different properties and activities. Such conjugates may be formulated with acceptable carriers, diluents, and additives for use, for example, in biodetection, diagnostics, agriculture and pharmaceuticals.

The modified branched polymer labeling conjugates are suitable for use in a variety of applications where specific delivery of bioactive materials is desired. In a preferred embodiment of the present invention, the modified branched polymer conjugates are comprised of one or more modified branched polymers associated with one or more bioactive materials.

In another aspect of the invention, the modified symmetrically branched polymer has regular symmetrical branch junctures within the polymer. In another aspect of the invention, the asymmetrically branched polymer has either random or regular, asymmetrical branch junctures with a mixture of terminal and chain branching patterns.

In another aspect of the invention, the modified symmetrically branched polymer has functional groups predominantly at the exterior. In another aspect of the invention, the asymmetrically branched polymer has functional groups both at the exterior and in the interior.

In yet another aspect of the invention, the modified symmetrically branched polymer has an interior void space.

In a further aspect of the invention, the asymmetrically branched polymer has unevenly distributed void spaces.

In another aspect of the invention, the symmetrically branched polymer, as defined above, including, but not limited to polyethyleneimine dendrimers, polypropyleneimine dendrimers, polyether dendrimers, polyester dendrimers, combbranched/starbranched polymers such as polyethyleneoxide, polyethyleneglycol, polymethyloxazoline, polyethyloxazoline, polymethylmethacrylate, polystyrene, polybutadiene, polyisoprene, polydimethylsiloxane, combbranched dendrigrafts such as polyethyloxazoline, polyethyleneimine, and polystyrene, and so on is modified with at least one monomer capable of forming new functional groups and/or additional branches at a given time so that new material properties is achieved.

The modified symmetrically branched polymers can be either obtained through chemically linked functional groups on, for example, symmetrically branched polypropyleneimine dendrimers (commercially available from Aldrich), polyether dendrimers, polyester dendrimers, combbranched/starbranched polymers such as polyethyleneoxide, polyethyleneglycol, polymethyloxazoline or polyethyloxazoline, polystyrene, and combbranched dendrigrafts such as polyethyloxazoline, polyethyleneimine, and polystyrene.

The synthetic procedures for these symmetrically branched polymers/dendrimers are known (see "Dendrimers and Other Dendritic Polymers", edited by J M J Frechet and D A Tomalia, John Wiley & Sons, Ltd., 2001).

In another aspect of the invention, the asymmetrically branched polymer is modified with at least one monomer capable of forming additional branches at a given time so that new material properties can be achieved, wherein the said modified polymer is defined as a modified asymmetrically branched polymer.

The modified asymmetrically branched polymers can be either obtained, for example, through chemically linked functional groups on regular asymmetrically branched polylysines or on random asymmetrically branched polyethyleneimines (commercially available from Aldrich, Polysciences, or BASF under the trade name, Luposal™).

The random asymmetrically branched polyoxazoline polymers can be prepared according to procedures described by M Litt (J. Macromol. Sci. Chem. A9(5), pp. 703-727 (1975)).

In another aspect of the invention; the branched polymers/dendrimers are further modified with functional groups, such as, but not limited to an $—NH_2$, —NHR, $—NR_2$, $—NR_3^+$, —COOR, —COOH, —COO—, —OH, —C(O)R, —C(O)$NH_2$, —C(O)NHR, or —C(O)$NR^2$ group, an aliphatic group, which can be branched, contain one or more double and/or triple bonds and/or may be substituted, an aromatic group, which may contain a plurality of rings, which may be fused or separated, the rings may be of varying size and/or may contain substituents, perfluorocarbon chains, saccharides, which may be of varying ring sizes, the rings may contain a heteroatom, such as a sulfur or nitrogen atom., and/or may be substituted, polysaccharides, containing two or more monomers, may be branched and/or may be substituted, and polyethylene glycols, wherein R can be any aliphatic or aromatic group, or a combination thereof.

The molecular weight of the non-modified and modified branched polymers can range from about 500 to over 5,000,000; preferably from about 500 to about 1,000,000; more preferably from about 1,000 to about 500,000; and more preferably from about 2,000 to about 100,000.

The preferred labeling conjugates of the present invention include those where a branched polymer labeling conjugate comprises at least one modified branched polymer associated with at least one unit of at least one biologically active (bioactive) material. Some examples of biologically active materials are molecules with a binding activity, but not a molecule used in assays as mobile elements to bind target molecules, such as a primary antibody. Thus, the conjugates of interest are usable in what are known as "indirect" immunoassays.

Suitable such binding molecules include hormones and receptors therefor; lectins and the cognate carbohydrate; avidin, streptavidin, or neutravidin and biotin; antigen and antibody, such as fluorescein and anti-fluorescein; enzyme and co-factor or substrate; antibody and anti-antibody and so on.

In one aspect of the invention, the modified branched polymer-bioactive material conjugates can be utilized, for example, for the rapid detection of target molecules of interest, such as environmental pollutants, chemical and biological warfare agents, as well as for screening for drug targets and leads, and therapeutic drug and therapeutic effect monitoring.

In another aspect of the invention, the modified asymmetrically or symmetrically branched polymer-bioactive material conjugates can be utilized, for example, for the rapid diagnosis of different cancers, tumors, pathological states and diseases, as well as for monitoring biomarker changes and protein profiling during clinical trials and therapeutic treatments.

In another aspect of the invention, the modified branched polymer-bioactive material conjugates can be utilized, for example, for the construction of, for example, indirect sandwich and sequential assays, using a labeling reagent that does not bind directly to the target analyte.

In another aspect of the invention, the modified branched polymer-bioactive material conjugates can be utilized, for example, for the construction of, for example, nucleic acid, DNA, or RNA based assays, using a labeling reagent that directly or indirectly bind to the target analyte.

In another aspect of the invention, the modified branched polymer-bioactive material conjugates are capable of carrying a variety of metal ions for both in vitro/in vivo imaging and radiotherapy related applications. Such conjugates could also be used in conjunction with a nano/microparticle so that it could serve as a better drug delivery and therapeutic vehicles for certain disease treatment. These nano/microparticles can either be biodegradable or non-biodegradable.

In yet another aspect of the invention, at least one modified branched polymer can be utilized to carry at least one biologically active molecule to various solid surfaces, generating virtually no denaturation of the at least one biologically active molecule at the surface. These surfaces include labeling or reporter molecules, such as latex beads, metal sols and so on. The branched polymers can be used to affix capture molecules to a solid phase, such as a membrane, a plastic surface and the like.

The modified branched polymer labeling conjugates may be further used in applications related to agriculture, food safety assurance, as well as in vitro and in vivo diagnostics and targeting. Such conjugates may be utilized as key sensing components in various sensor platforms including, but not limited to, optical, electrical, piezoelectric devices, as well as microfluidics and microelectromechanical systems (MEMS) and nanoelectromechanical systems (NEMS).

Additional features and advantages of the present invention are described in, and will be apparent from, the following Detailed Description of the Invention and the figures.

BRIEF DESCRIPTION OF THE FIGURES

The following description of the figures and the respective drawings are non-limiting examples that depict various embodiments that exemplify the present invention.

FIG. 8A provides a configuration of an immunoassay ticket without a plastic cover; FIG. 8B provides another configuration of an immunoassay ticket without a plastic cover; FIG. 8C provides yet another configuration of an immunoassay ticket without a plastic cover; FIG. 8D provides another configuration of an immunoassay ticket without a plastic cover; FIG. 8E provides a configuration of an immunoassay ticket without a plastic cover where all of the elements except for the liquid receiving pad are on the same membrane; FIG. 8F provides another configuration of an immunoassay ticket without a plastic cover; and FIGS. 8G and 8H provide a configuration of an immunoassay where all of the elements except for the liquid receiving pad are on the same membrane. The dipstick and lateral flow assays, with or without a cover, work in a similar manner.

DETAILED DESCRIPTION OF THE INVENTION

Figure 1:
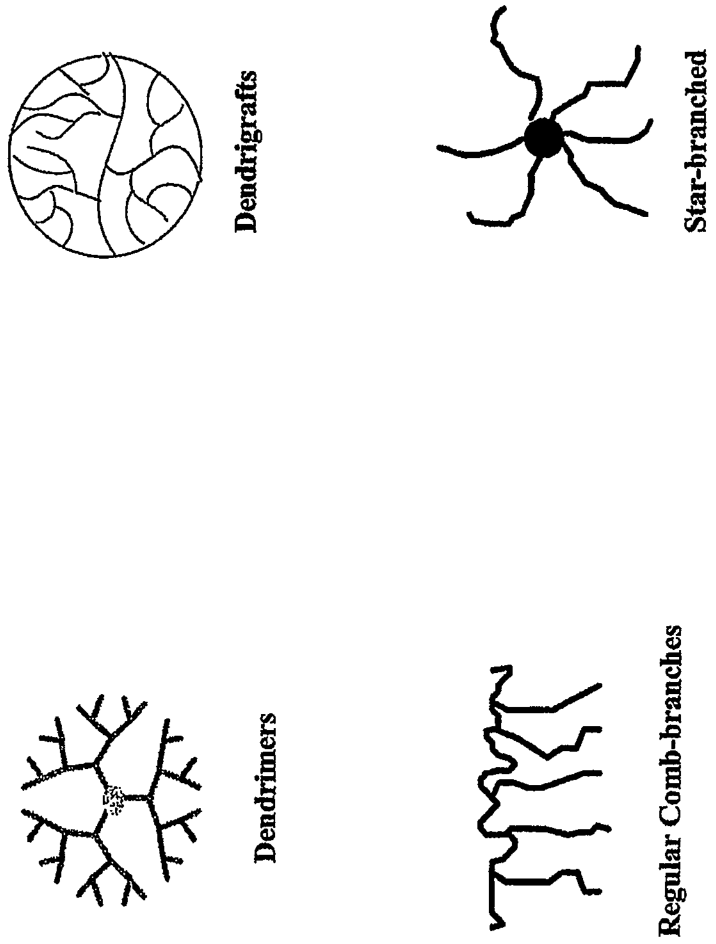
FIG. 1 depicts symmetrically branched polymers including a dendrimer, a dendrigraft, a star-shaped polymer, a comb-shaped polymer.

Symmetrically branched (SB) polymers are depicted in FIG. 1, with symmetric branches, wherein all the polymers of interest possess a core and exhibit symmetrical branch junctures consisting of either terminal or chain branches throughout the entire polymer. The functional groups are present predominantly at the exterior.

Figure 2:
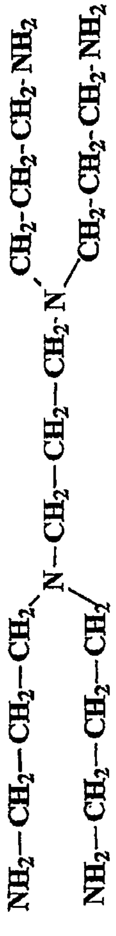
FIG. 2 depicts the chemical structure of symmetrically branched polypropyleneimine dendrimers.
Figure 2:
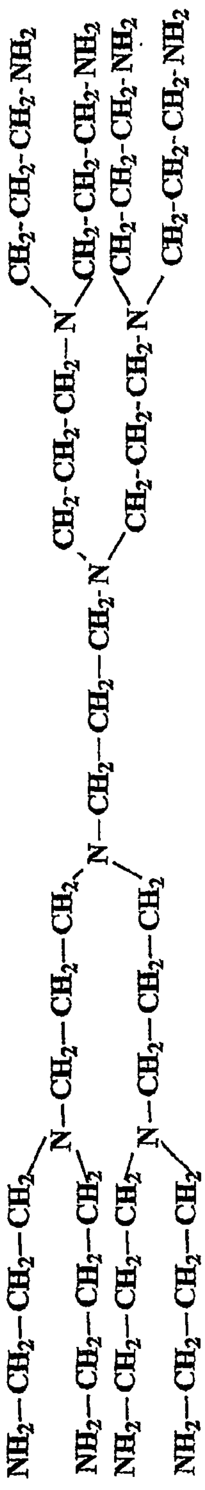
Figure 3:
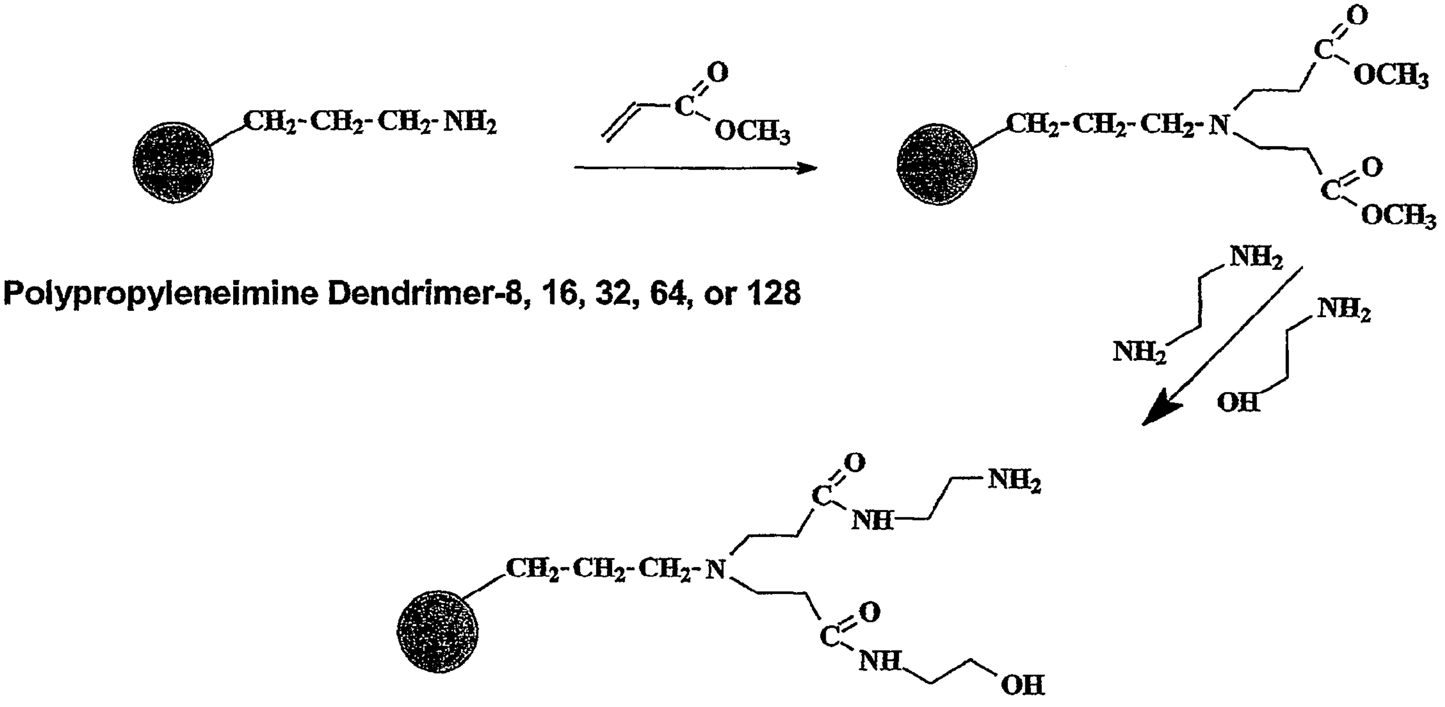
FIG. 3 depicts chemical modification reactions of symmetrically branched polypropyleneimine dendrimers. The numbers, 8, 16, 32, . . . , indicate the number of reactive groups at the surface of the dendrimer.

Such polymers exhibit a number of unique advantages. First, a number of symmetrically branched polymers are commercially available (i.e. various generations of polypropyleneimine dendrimers, FIG. 2) or can be produced readily with commercially available monomers using synthetic procedures (see "Dendrimors and Other Dendritic Polymers", edited by J M J Freshet and D A Tomalia, John Wiley & Sons, Ltd., 2001).

The synthesis of combbranched and combburst polymers is known (see Tomalia's U.S. Pat. No. 5,773,527 and Yin's U.S. Pat. Nos. 5,631,329 and 5,919,442).

Second, due to higher branching densities, symmetrically branched polymers are often more molecularly compact. Third, the well defined interior void space also made them ideal as a carrier for entities, such as reporter molecules entrapped or encased therein.

The symmetrically branched polymers often can be modified for biological and medical related applications. As new and more biofriendly monomers are added, the properties of the resulting modified symmetrically branched polymers also change significantly. For example, on modification, a water insoluble SBP can become completely water soluble, while a SBP with a high charge density can be modified to carry very low or no charges on the polymer.

In one embodiment of this invention, the symmetrically branched polymer (for example, either a symmetrically branched polyethyleneimine (PEI) dendrimer, polypropyleneimine (PPI) dendrimer or a symmetrically branched PEI dendrigrafts) was modified with different kinds of primary amine groups through, for example, Michael addition or an addition of acrylic esters onto amines of the polymer. Thus, for example, through a Michael addition reaction, methyl acrylate can be introduced onto the primary and/or secondary amino groups of polyethyleneimine and polylysine polymers. The ester groups then can be further derivitized, for example, by an amidation reaction. Thus, for example, such an amidation reaction with, for example, ethylenediamine, can yield the addition of an amino group at the terminus of the newly formed branch. Other modifications to the polymer can be made using known chemistries, for example, as provided in "Poly(amines) and Poly(ammonium salts)" in Handbook of Polymer Synthesis (Part A) Edited by H R Kricheldorf, New York, Marcel Dekker, 1994 and "Dendrimers and Other Dendritic Polymers", edited by J M J Frechet and D A Tomalia, John Wiley & Sons, Ltd., 2001.

On such addition, a modified symmetrically branched polymer, such as, a modified PEI, PPI dendrimer, or PEI dendrigraft, is formed. As an extension of the symmetrically branched polymer, such as PPI and PEI, the resulting modified OP is also symmetrically branched. Depending on the solvent environment (i.e. pH or polarity), the surface functional groups can carry different charges and charge densities. The molecular shape and functional group locations (i.e., functional group back folding) can then be further tuned, based on these characteristic properties.

In another embodiment of this invention, the modified symmetrically branched polymers can be produced using any of a variety of synthetic schemes that, for example, are known to be amenable to reaction with a suitable site on the polymer. Moreover, any of a variety of reagents can be used in a synthetic scheme of choice to yield any of a variety of modifications, or additions to the polymer backbone. Thus, for example, in the case of the Michael addition reaction to an amine described above, the addition of any of a variety of monomers can be used at the alkylation stage with a $C_1$-$C_{22}$ acrylate. Preferred reactants, include methyl, ethyl, propyl, butyl, pentyl, hexyl, heptyl, octyl, nonyl, decyl, undecyl, dodecyl acrylate and mixtures thereof. Similarly, at the amidation stage in the example exemplified above, any of a variety of amines can be used. For example, ethylenediamine, monoethanolamine, tris(hydroxymethyl)aminomethane, alkyl amine, allyl amine, or any amino modified polymers including polyethylene glycol (PEG), perfluoropolymers, polystyrene, polyethylene, polydimethylsilixane, polyacrylate, polymethylmethacrylate, and the like, and mixtures thereof, can be used.

That synthetic strategy would allow not only symmetric growth of the molecule, where more branches with different chemical compositions can be readily introduced, but also the addition of multiple functional groups at the exterior of the structure. Obviously, one can continuously modify the precursor polymer using the same or a different synthetic process until the desired symmetrically branched polymers with appropriate molecular weights and functional groups are attained. In addition, the hydrophobic and hydrophilic properties, as well as charge densities of such polymers, can be readily tailored to fit specific application needs using appropriate monomers for constructing the polymer, and suitable modification reactions.

In another embodiment of the invention, if a divergent synthetic procedure is used, the chain end of symmetrically star- or comb-branched polyoxazoline, polyethyleneimine, polyethyleneoxide/glycol, or polystyrene can be modified with another small molecule to generate various functional groups at the polymeric chain ends including primary, secondary or tertiary amines and carboxylate, hydroxyl, alkyl, fluoroalkyl, aryl, PEG, acetate, amide, and/or ester groups. Alternatively, various initiators can also be utilized so that the same type of functional groups can be introduced at the chain end, if a convergent synthetic approach is utilized (Dendritic Molecules, edited by G R Newkome et al., VCH, Weinheim, 1996, Dendrimers and Other Dendritic Polymers, edited by J M J Frechet and D A Tomalia, John Wiley & Sons, Ltd., 2001, J. Macromol. Sci. Chem. A9(5), pp. 703-727 (1975)) and "Dendrimers and Other Dendritic Polymers", edited by JMJ Frechet and DA Tomalia, John Wiley & Sons, Ltd., 2001.

Figure 4:
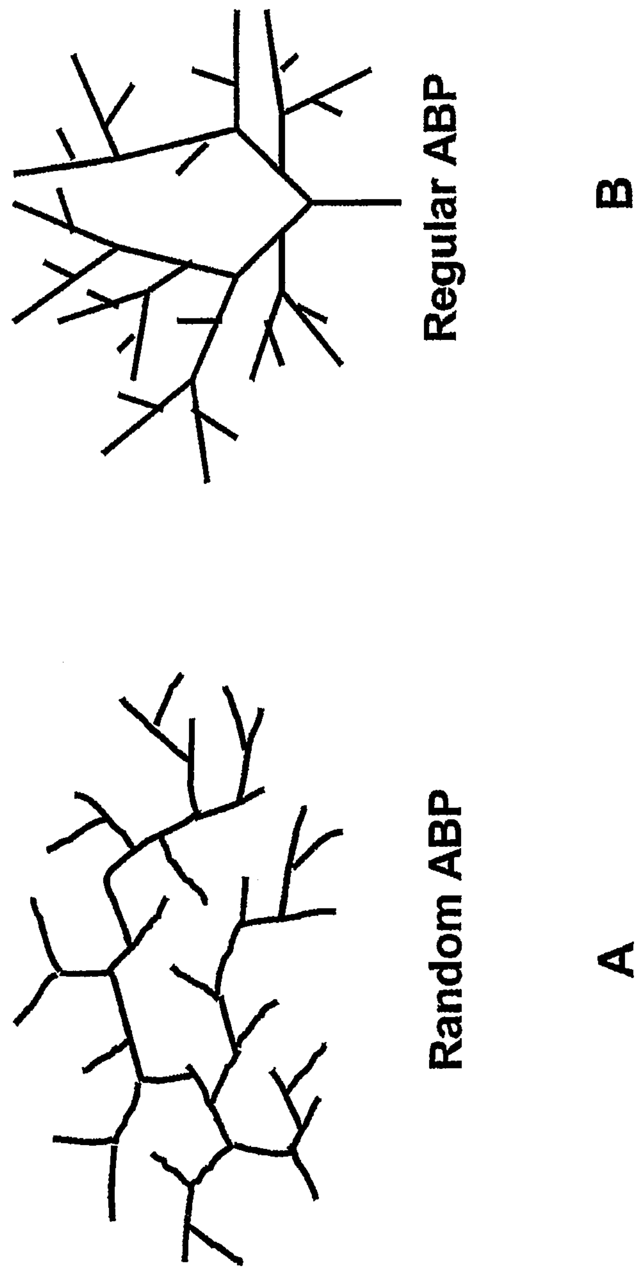
FIG. 4 depicts random (A) and regular (B) asymmetrically branched polymers with asymmetrical branch junctures and patterns.

Asymmetrically branched polymers are depicted in FIG. 4, with asymmetric branches, wherein some of the polymers of interest possess no core and exhibit asymmetrical branch junctures consisting of both chain and terminal branches throughout the entire polymer. The functional groups are present both at the exterior and in the interior.

Such polymers exhibit a number of unique advantages. First, a variety of known starting materials can be employed. Such monomers and polymers are low-cost and very easy to manufacture in large quantities. For example, one such precursor polymer that can be used to synthesize a polymer of interest is PEI. The synthesis of random asymmetrically branched polyethyleneimines is known (GD Jones et al., J. Org. Chem. 9, 125 (1944)) and the synthetic procedures for these precursor polymers are well established. Polyethyleneimines with various molecular weights are commercially available from different sources such as Aldrich, Polysciences, and BASF (under the trade name Luposal™). The random asymmetrically branched polyethyleneimines are primarily produced through cationic ring-opening polymerization of ring-strained cyclic imine monomers, such as aziridines (ethyleneimine) and azetidines (propyleneimine), with Lewis or Bronsted acids as initiators. (OC Definer et al, "Ethylenediamine and Other Aziridines", Academic Press, New York, (1969), and A S Pell, J. Chem. Soc. 71 (1959)). Since it is a one-pot process, large quantities of random asymmetrically branched polymers can be readily produced.

The randomly branched poly(2-substituted oxazoline) polymers can be prepared according to procedures described by M Litt (J. Macromol. Sci. Chem. A9(5), pp. 703-727 (1975)).

Second, the prior art synthetic processes often generate various branch junctures within the macromolecule. In other words, a mixture of terminal and chain branch junctures is distributed throughout the entire molecular structure. The branching densities of these random asymmetrically branched polymers are lower, and the molecular structure is more open when compared with dendrimers and dendrigrafts. Although the branch pattern is random, the average ratio of primary, secondary, and tertiary amine groups is relatively consistent, with a ratio of about 1:2:1, as described by C R Dick et al, J. Macromol. Sci, Chem., A4 (6), 1301-1314 (1970) and G M Lukovkin, Eur. Polym, J. 9, 559 (1973).

Due to the presence of these branch junctures, the random asymmetrically branched polyethyleneimines are still considered spherical macromolecules. Within the globular structure, there are various sizes of pockets formed from the imperfect branch junctures at the interior of the macromolecule. Unlike dendrimers and dendrigrafts where interior pockets are always located around the center core of the molecule, the pockets of random asymmetrically branched polymers are spread unevenly throughout the entire molecule. As a result, random asymmetrically branched polymers possess both exterior and unevenly distributed interior functional groups that can be further reacted with a variety of molecules, thus forming new macromolecular architectures, defined as modified random asymmetrically branched polymers.

Although having a core, the functional groups of the regular asymmetrically branched polymer are also distributed both at the exterior and in the interior, which is very similar to the random ABP. Again, a variety of precursor polymers can be used to construct such polymers of interest. One such precursor polymer is polylysine. The best example of making such polymers is regular asymmetrically branched polylysine polymers as described in U.S. Pat. Nos. 4,289,872; 4,360,646; and 4,410,688. As a result, such polymers can also be modified in a similar manner as for the random ABPs.

In one embodiment of this invention, the asymmetrically branched polymer (for example, either a random asymmetrically branched polyethyleneimine (PEI) or a regular asymmetrically branched polylysine) was modified with different kinds of primary amine groups through, for example, Michael addition or an addition of acrylic esters onto amines of the polymer. Thus, for example, through a Michael addition reaction, methyl acrylate can be introduced onto the primary and/or secondary amino groups of polyethyleneimine and polylysine polymers. The ester groups then can be further derivitized, for example, by an amidation reaction. Thus, for example, such an amidation reaction with, for example, ethylenediamine, can yield the addition of an amino group at the terminus of the newly formed branch. Other modifications to the polymer can be made using known chemistries, for example, as provided in "Poly(amines) and Poly (ammonium salts)" in Handbook of Polymer Synthesis (Part A) Edited by H R Kricheldorf, New York, Marcel Dekker, 1994.

On such addition, a modified asymmetrically branched polymer, such as, a modified PEI or polylysine polymer, is formed. As an extension of the asymmetrically branched polymer, such as PEI and polylysine, the resulting modified ABP is also asymmetrically branched. Depending on the solvent environment (i.e. pH or polarity), the surface functional groups can carry different charges and charge densities. The molecular shape and functional group locations (i.e., functional group back folding) can then be further tuned, based on these characteristic properties.

In another embodiment of this invention, the modified asymmetrically branched polymers can be produced using any of a variety of synthetic schemes that, for example, are known to be amenable to reaction with a suitable site on the polymer. Moreover, any of a variety of reagents can be used in a synthetic scheme of choice to yield any of a variety of modifications, or additions to the polymer backbone. Thus, for example, in the case of the Michael addition reaction to an amine described above, the addition of any of a variety of monomers can be used at the alkylation stage with a $C_1$-$C_{22}$ acrylate. Preferred reactants, include methyl, ethyl, propyl, butyl, pentyl, hexyl, heptyl, octyl, nonyl, decyl, undecyl, dodecyl acrylate and mixtures thereof. Similarly, at the amidation stage in the example exemplified above, any of a variety of amines can be used. For example, ethylenediamine, monoethanolamine, tris(hydroxymethyl)aminomethane, alkyl amine, allyl amine, or any amino modified polymers including polyethylene glycol (PEG), perfluoropolymers, polystyrene, polyethylene, polydimethylsilixane, polyacrylate, polymethylmethacrylate, and the like, and mixtures thereof, can be used.

This synthetic strategy would allow not only asymmetric growth of the molecule, where more pockets can be readily introduced, but also the addition of multiple functional groups at both the interior and the exterior of the structure. Obviously, one can continuously modify the precursor polymer using the same or a different synthetic process until the desired asymmetrically branched polymers with appropriate molecular weights and functional groups are attained. In addition, the hydrophobic and hydrophilic properties, as well as charge densities of such polymers, can be readily tailored to fit specific application needs using appropriate monomers for constructing the polymer, and suitable modification reactions.

In another embodiment of the invention, the chain end of random asymmetrically branched polyoxazoline can be terminated or reacted with another small molecule to generate various functional groups at the polymeric chain ends including primary, secondary or tertiary amines and carboxylate, hydroxyl, alkyl, fluoroalkyl, aryl, PEG, acetate, amide, and/or ester groups. Alternatively, various initiators can also be utilized so that the same type of functional groups can be introduced at the chain end (J. Macromol, Sci, Chem. A9(5), pp. 703-727 (1975)). Therefore, an alkyl modified, random asymmetrically branched poly(2-ethyloxazoline) with primary amine chain ends can be prepared using M Litt's procedure, supra.

In another embodiment of this invention, modified branched polymers can be utilized to carry bioactive materials for both in vitro and in vivo related applications. The bioactive materials comprise a variety of molecules, particularly those with the ability to bind another molecule, such as a biological polymer, such as a polypeptide, or a polysaccharide, an enzyme, a receptor, a vitamin, a lectin, metals, metal ions and so on. Metals and metal ions that can be carried by a polymer of interest may include, but are not limited to, transition metals and others, such as Sc, Y, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd Hg, Ga, In, Ti, alkali metals, alkaline-earth metals, Lanthanide series elements, such as Ce, Pr, Nd, Pm, Sm, Eu, Gd, Tb, Dy, Ho, Er, Tm, Yb and Lu, and Actinide series elements, such as Tb, Pa, U, Np, Pu, Am, Cm, Bk, Cf, Es, Fm, Md, No, and Lr. With the attachment of one or more chelating groups, including, but not limited to, ethylenediaminetetraacetic acid (EDTA), diethylenetriaminepentaacetic acid (DTPA), diethylenetriaminepentaacetic acid (DTPA), 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N (2-aminoethyl)pamide and DOTA-N-(2-aminophenethyl) amide on a modified branched polymer, metal ions, such as those selected from Sc, Y, Ti, Zr, Hf, V. Nb, Ta, Cr, Mo, W, Mn, Tc, Re, Fe, Ru, Os, Co, Rh, Ir, Ni, Pd, Pt, Cu, Ag, Au, Zn, Cd Hg, Ga, in, Ti, alkali metals, alkaline-earth metals, Lanthanide series elements, such as Co, Pr, Nd, Pm, Sm, Eu, Gd, Tb, Dy, Ho, Er, Tm, Yb and Lu, and Actinide series elements, such as Th, Pa, LT, Np, Pu, Am, Cm, Bk, Cf, Es, Fm, Md, No, and Lr, can be chelated onto the polymer. Such metal loaded polymer can then be covalently or non-covalently attached onto a nano or microparticle prepared from both inorganic and organic/polymeric materials. The nano/microparticles either can be biodegradable or non-biodegradable. Alternatively, the chelating groups can be linked with an intermediate linker such as a biotin, white the modified branched polymer is covalently attached to a streptavidin, avidin, or neutravidin. The nano/microparticle can first be functionalized with a polymer-streptavidin conjugate, followed by reaction with either biotinylated chelating groups or metal ion loaded biotinylated chelating groups. The nano/microparticle-polymer-chelating-metal ion conjugates can be used for both in vitro and in vivo diagnostic/imaging purposes, as well as in vivo medical treatment applications, including, but not limited to radiotherapy, immunotherapy, gene, cell therapy, or a combination thereof, and so on.

For in vivo imaging purposes, a conjugate of interest comprises a reporter molecule that can be detected by an external device, such as a gamma camera. Thus, a conjugate is configured to comprise a radioisotope that will emit detectable radiation. The conjugate is placed into a format suitable for consumption or placement in a body, employing reagents suitable therefor as known in the art. The conjugate composition is administered as known in the art, such as orally, rectally, intravenously and so on, and the conjugate is configured in a composition suitable for the route of administration.

The labeled molecule of interest can serve as a diagnostic agent. By "diagnostic agent" is meant a molecule which can be used as a marker for a particular disease, physiological state or stage, a pathological stage or state, and so on. Albumin, mineral level, microorganism, specific antibody, specific antigen, toxin and so on are examples of diagnostic agents. Therapeutic agents are those that confer a beneficial effect, such as a drug, a nutrient, a protein, a medical device consisting of a drag, a nutrient, and/or a protein, and so on.

For the purposes of the instant invention, a "detector molecule" is a molecule with a binding activity. The detector molecule is used in an assay herein for binding to a target molecule or analyte. A purpose of an assay of interest is to determine the presence, and optionally the amount of, said target molecule or said analyte in a sample. Examples of detector molecules include antibodies, and antigen binding portions thereof, receptors and so on. Any molecule taught herein and known in the art as binding to another entity can be used as a detector molecule.

The detector molecule is not labeled with a detectable reporter molecule, or as used equivalently herein, a detectable label. The detectable reporter molecule is meant to be a molecule that provides a detector molecule that can be traced without further intervention, such as chemical intervention, such as exposing the detector reporter which is an enzyme to an enzyme substrate. Thus, a detector molecule of interest is not one which is directly labeled, such as an antibody conjugated to a gold sol. Preferably, the detector molecule is not manipulated or conjugated in any way, and is used as a native reagent or molecule. However, in some embodiments, the detector molecule can be tagged with a member of a binding pair, such as, for example, a biotin molecule. Thus, the detector molecule carrying the member of a binding pair can be bound by the other member of a binding pair, for example, in the case of biotin, avidin, which can in turn be bound to the detectable label.

The biologically active material is one that has a recognition or binding ability. For the purposes of the instant invention, those molecules of interest that have a recognition or binding ability are identified as binding pairs, or individually as one of or one member of a binding pair. Thus, examples of binding pairs include an antibody and an anti-antibody; the $F_c$ portion of an antibody and an $F_c$ receptor; avidin, streptavidin, neutral avidin, NeutraLite avidin or other avidin derivatives and analogs, and biotin; antigen and antibody, such as albumin and anti-albumin, a hapten, such as dinitrophenol (DNP) and antibody to the hapten, such as, anti-DNP and so on, hormone receptor and hormone; nucleic acid binding moiety, such as a protein and a target nucleic acid, such as a restriction enzyme; enzyme and substrate; enzyme and cofactor; one strand of a nucleic acid and the complementary strand of nucleic acid; enzyme and nucleic acid recognition site, as with restriction enzymes; lectin and the cognate saccharide; and so on. Any set of molecules that exhibit a specific binding reaction where the binding therebetween can be exploited for detecting presence or one or the other can be used in the practice of the instant invention.

The joining of a polymer of interest with another molecule of interest, such as a bioactive molecule, such as a protein, such as streptavidin, colloidal gold and the like, is carried out using known methods, such as, chemical synthetic methods using the chemical characteristics of the modified branched polymer (MBP) and of the molecule to be bound thereto. Thus, the modified branched polymer can contain, for example, amine groups that can be used as the reactive site to which a molecule of interest can be bound through covalent linkages. Alternatively, the joining may occur by mere mixing of the polymer and molecule to be bound through non-covalent linkages therebetween. The linking of another entity to the polymer of interest can also be achieved through a combination of both. For example, a polymer of interest can be covalently linked to a bioactive material, followed by physical adsorption of a reporter particle through non-covalent linkages to form a bioactive material-polymer-reporter particle conjugate, which can be readily used for bioassays.

One form of an antibody-based "sandwich" assay consists of four components: a capture antibody, an antigen, a detector antibody for binding the target and a labeled reporter molecule of interest which binds to the detector antibody. The reporter can be an enzyme, a fluorophore, a colored particle, a dyed particle or a particle containing a dye, a stained particle, a radioactive label, quantum dots, nanocrystals, up-converting phosphorescent particles, metal sols, fluorophore or dye-containing polymer or latex beads that are detectable visually and/or with mechanical assistance and so on. Such an assay often requires three separate experimental steps. The first step involves immobilization of the capture antibody and reversibly binding the detector antibody on a solid surface, followed by a subsequent addition of an antigen solution to form an antibody-antigen complex. The last step is to add a reporter group comprising a labeled detector molecule or structure to generate a capture antibody-antigen-detector antibody reporter complex. In the case of a one-step assay, such as a lateral flow or capillary assay, the reporter is reversibly affixed to the solid surface in a region either before or after where detector antibody contacts antigen and a region before where the immobilized capture antibody is located. As a result of this "sandwich" assay, the unknown antigen can be identified, as well as the quantity and concentration of the antigen, which can be quantified, for example, with an optical reader. If the antigen is not present in the sample solution, no "sandwich" complex will be formed, and thus no signal will be observed.

The capture antibody can be affixed to a solid surface using an MBP of interest. Any binding molecule used to separate free from bound in an assay of interest can be bound to a solid phase using an MBP of interest.

The actual structure of "sandwich" complexes is highly dependent on the binding reagents and reporter moieties. The various assay formats can be exemplified using, for example, colloidal gold as the reporter molecule. It is well known in the art that the formation of capture antibody-antigen-detector antibody-gold particle complexes results in a discernable positive test. Alternatively, the detector antibody can be replaced with another non-antibody binding molecule suitable for binding the target.

The modified branched polymer (MBP) based assays of interest generate a clean immunocomplex: capture antibody-antigen-detector antibody-MBP-particle; MBP-capture antibody-antigen-detector antibody-particle; or MBP-capture antibody-antigen-detector antibody-MBP-particle. In this case, only a clean immunocomplex is formed, and pre-crosslinked products contributing to background are eliminated. As a result, the assay sensitivity is significantly enhanced, and false positive readings are dramatically reduced. In addition, much smaller amounts of reagents are utilized when compared with standard direct-labeled antibody-based assays that do not employ the polymers of interest. This approach is independent of dipole moment and isoelectric point of proteins, thus greatly simplifying assay construction processes and all the while maintaining the protein of interest in native configuration or at the least, in a configuration that maintains particular binding sites and epitopes of interest.

Another assay configuration is based on a sequential assay format for the detection of antibodies in unknown samples. In this case, an antigen or fragment thereof carrying an epitope is applied to the solid surface. During the test, the antigen will bind with the detector antibody, which subsequently reacts with another generic anti-species antibody which is either directly or indirectly labeled with a reporter, for example, comprising colloidal gold. Therefore, the characteristic red color indicates a positive test, while no color change indicates a negative test. A polymer of interest also can be used to affix the antigen to the solid phase, as well as used to label an antibody of interest as described hereinabove.

Yet another assay configuration is another sandwich assay format. A capture antibody is applied to the membrane surface, optionally via an MBP. During the test, the capture antibody will bind with the targeted antigen, previously linked with an intermediate linker molecule, for example, a biotin or a fluorescein, which subsequently reacts with streptavidin or anti-fluorescein antibody labeled with colloidal gold or with unlabeled antigen present in a test sample. Therefore, the red color indicates a negative test, while no color change indicates a positive test. Again, a polymer of interest is used to attach proteins of interest to a solid phase and to mediate the labeling of proteins with a label, such as an additional reactant, such as the biotin or streptavidin, and the like.

Alternatively, the capture antibody can bind a complex which consists of antigen-detector antibody previously linked with an intermediate linker molecule, for example, a biotin, followed by reaction with streptavidin labeled with colloidal gold. A red color again indicates a positive test, while no color change indicates a negative test.

The capture antibody also can bind target antigen, followed by subsequent reaction with an antibody that detects or binds the capture antibody-antigen complex, previously linked with one member of a binding pair not specific for the target of the assay, for example, a biotin, which then reacts with a detectable label, whether direct or indirect, such as colloidal gold or an enzyme, respectively, labeled with the other member of the non-target binding pair, such as avidin or streptavidin.

Additionally, the capture antibody can bind a complex which consists of antigen-detector antibody, where the detecting antibody is previously linked with one member of a non-target binding pair, for example, a biotin, followed by reaction with a detectable label conjugated with the other member of the binding pair. A red color when using colloidal gold as the detectable label indicates a positive test, while no color change indicates a negative test.

Signal intensity and assay sensitivity can be enhanced by increasing the number of the one of the binding pairs attached to the detecting antibody. This can be achieved by incorporating, for example, multiple biotin or fluorescein molecules to the detecting antibody either directly or through a carrier molecule. That signal amplification also can be obtained, for example, by labeling with a plurality of reporter molecules or adding plural reporter molecules to a carrier which in turn is attached to the antibody, for example. The carrier molecule could be a small multi-functional molecule, a polymer, biomolecule such as protein, peptide, polysaccharide, DNA, RNA or a nanoparticle. Then, the carrier molecule loaded with a plurality of binding partner molecules is bound to a detecting antibody using standard methods.

Alternatively, plural binding pat titer molecules, for example, a detector antibody carrying plural biotin moieties and a detectable label or reporter molecule, such as an enzyme or colloidal gold particle, carrying plural avidin or streptavidin molecules, can be aggregated or polymerized and multiple molecules are attached to a multi-functional carrier molecule and the like to increase the number binding partner molecules bound to a single detecting antibody. Other means to obtain amplification of the signal apparatus can be used, as known in the art, the goal being to increase the signal of the complex at the capture site. That will increase assay sensitivity.

The separation of detecting antibody and detectable label can improve assay performance. Assay sensitivity is enhanced, fewer and lower amounts of reagents are needed, and manufacturing is simplified. That assay configuration overcomes the need to treat the detecting antibody to bind the detectable label which can lead to labeled antibody of poor yield, antibody with few bound label molecules, antibody with impacted specificity and so on. The separation of detecting antibody and detectable label may be further achieved by introducing a physical barrier between the reagents during detectable device construction.

In another embodiment, the reporter molecule is attached, optionally via an MBP, to a molecule that binds to the detector molecule, such as an antibody or antigen-binding portion thereof, that binds to the target or analyte to be determined in a sample. The reporter molecule can be, for example, a gold sol, optionally via an MBP, bound to, for example, an antibody that binds the detector molecule. Thus, for example, the detector antibody can be of a particular species and the report antibody can be one that binds antibodies of that particular species.

Alternatively, the molecule that binds the detector molecule can be bound, optionally via an MBP, to one of a binding pair, such as a biotin. The other of the binding pair, such as avidin, is bound, optionally via an MBP, to a reporter molecule, such as a gold sol.

Such configurations avoid the need to label or manipulate the detector molecule that binds the target or analyte in a sample. Several molecules that bind to a range of detector molecules can be optimized by conjugation as disclosed herein for use with any of a variety of primary detector molecules.

The instant assay can be configured as a qualitative assay, such as the commercially available pregnancy assay kits that yield a "yes/no" visible reaction. The instant assay also can yield quantitative results by providing graded amounts of reactants, suitable controls and a set of control reactions using known reagents to provide a "standard curve" to serve as a reference. Configuring an assay to provide quantitative results is known in the art with guidance obtainable in any of a variety of texts and publications.

Figure 7:
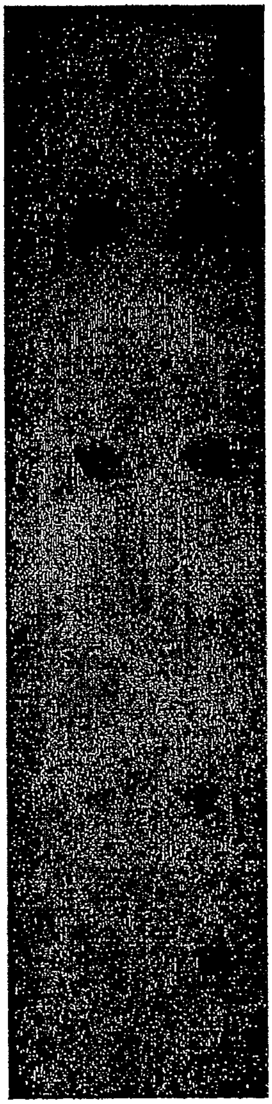
FIG. 7 illustrates an image of a positive microarray test for detecting multiple targets simultaneously.
Figure 8A:
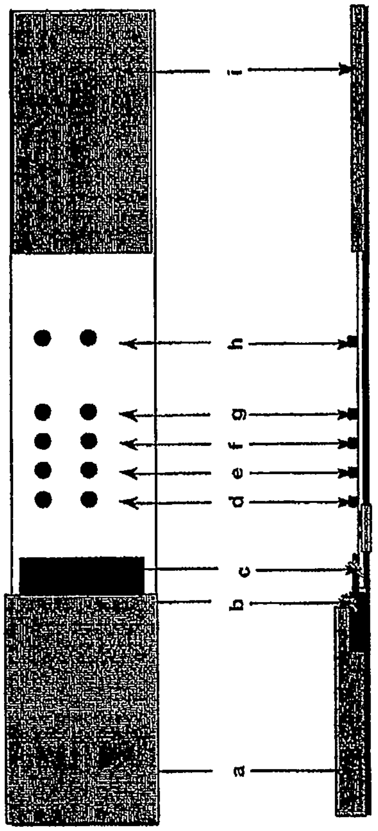
FIGS. 8A-8H illustrate lateral flow-based immunoassay configurations.
Figure 8B:
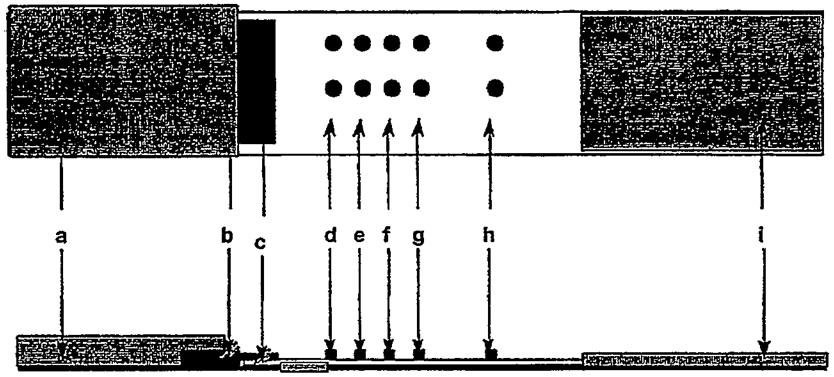
Figure 8C:
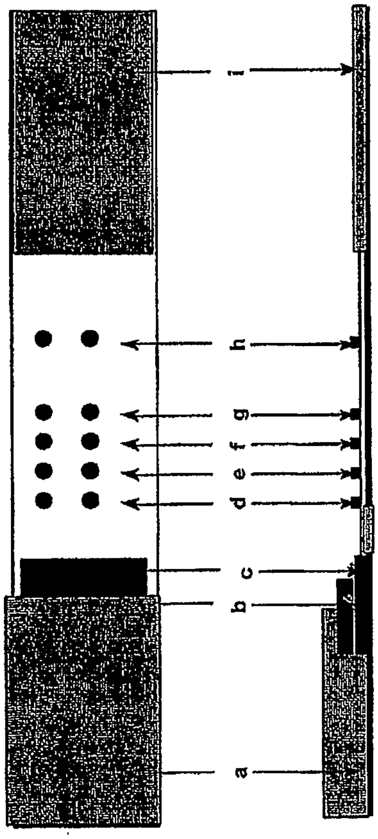
Figure 8D:
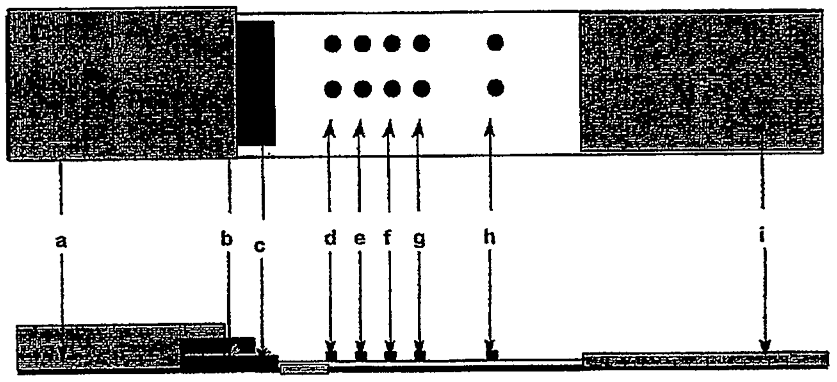
Figure 8E:
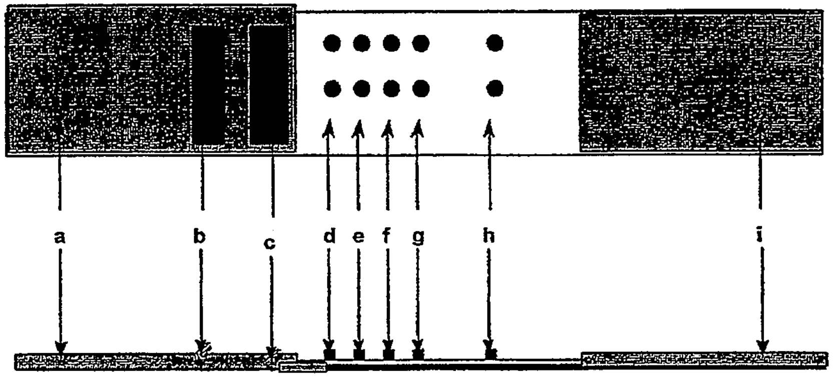
Figure 8F:
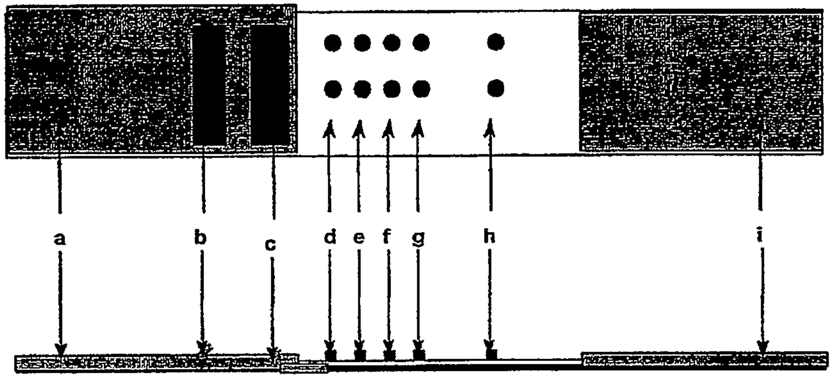
Figure 8G:
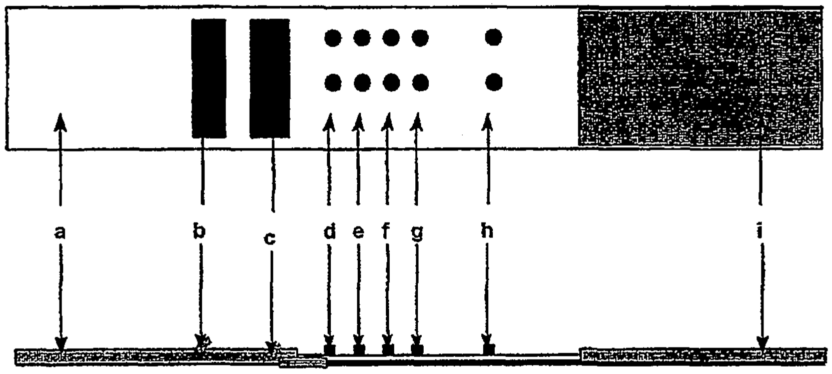
Figure 8H:
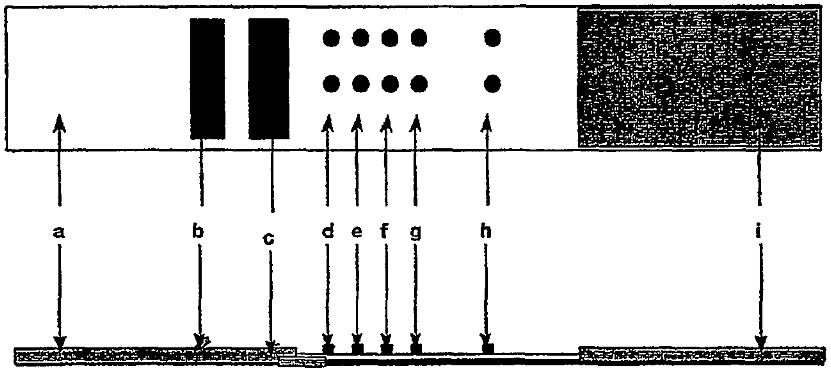

In one aspect of this invention, the modified branched polymer is covalently linked with a bioactive molecule (i.e. avidin or streptavidin). The resulting conjugate is allowed to react with colloidal gold particles. The resulting antibody-MBP-gold conjugate can be incorporated into a lateral flow immunoassay as depicted in FIGS. 7 and 8.

The modified branched polymer provides three unique features. First, the branched polymer serves as a spacer molecule between the reporter or binding pair and the solid surface or particle surface. Second, the branched polymer acts as a carrier to transport the bioactive molecules, as well as acting as an anchor to adhere those molecules onto a solid surface from a solution with only the branched polymer portion of the conjugate touching the surface. Third, during this anchoring process, the branched polymer-bioactive molecule conjugate also self-orients the complex at the solid surface.

Figure 9:
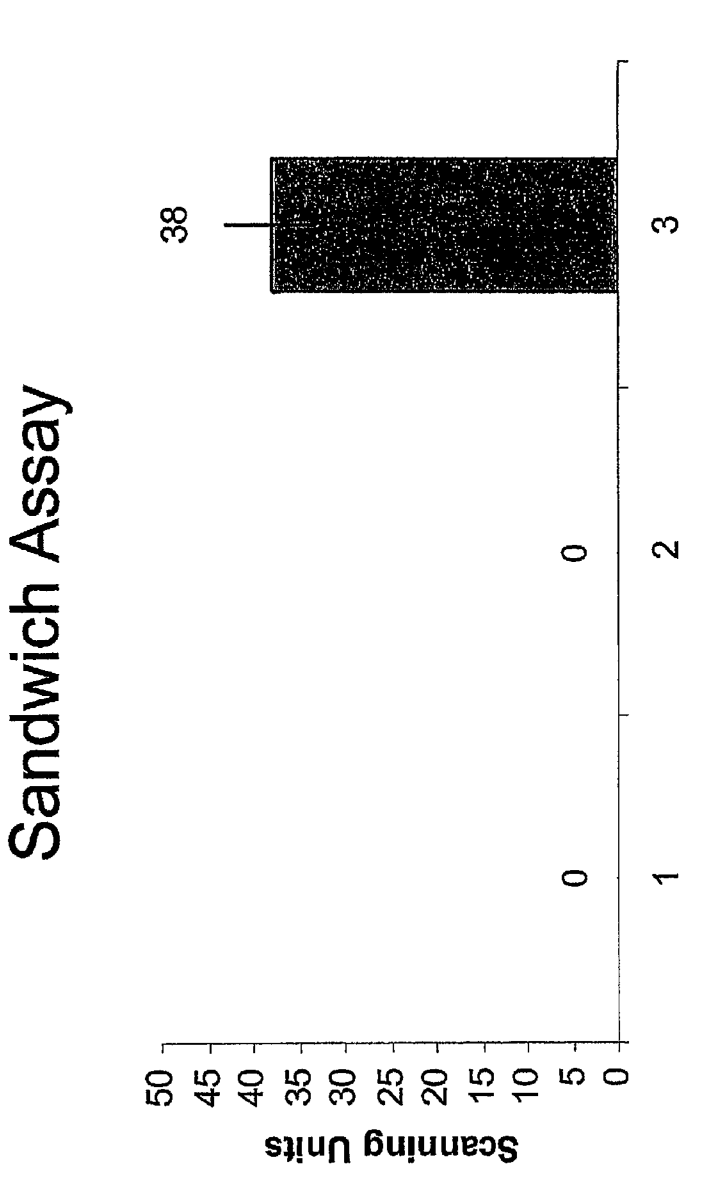
FIG. 9 illustrates results of a comparison test between non-polymer and polymer based lateral flow sandwich assays.
Figure 10:
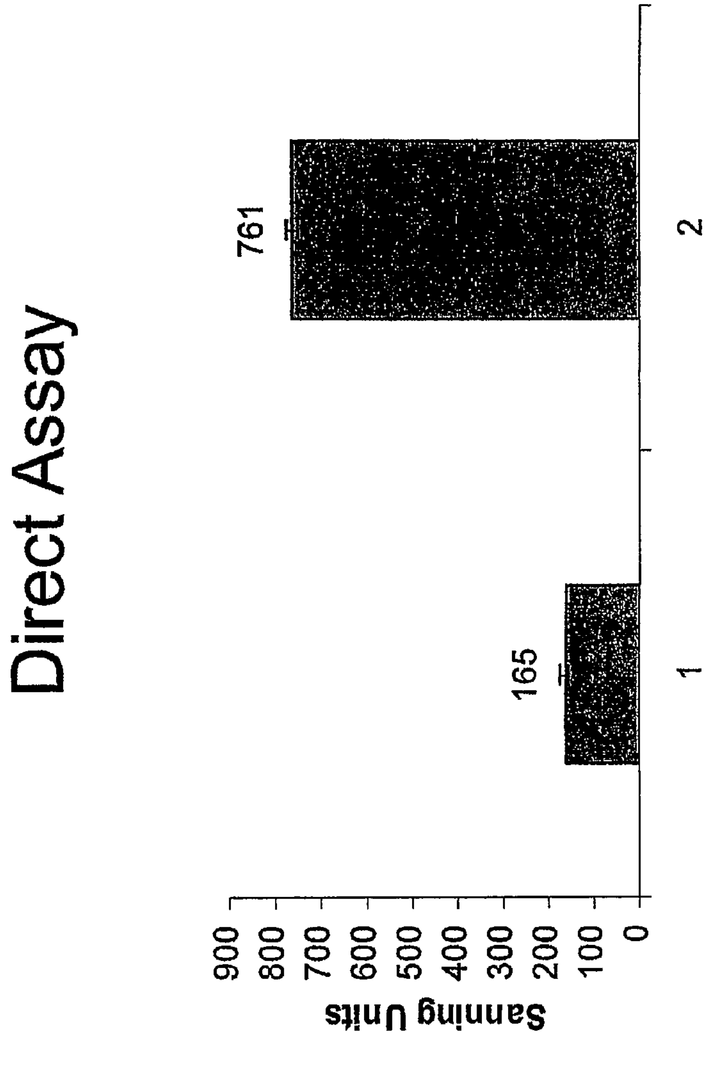
FIG. 10 illustrates results of a comparison test between non-polymer and polymer based lateral flow direct immunoassays.

As shown in FIGS. 9 and 10, the sensitivity of the polymer based lateral flow based sandwich and direct immunoassays are significantly enhanced over that of non-polymer based assays. In addition to the significant enhancement in sensitivities, the MBP-based lateral flow assays are also more amenable for medical diagnostics, target discovery, as well as monitoring biomarker changes and protein profiles during clinical trials and therapeutic treatments. The MBP-mediated fixation preserves biological structure and thus enhances stability and shelf life.

The conjugates of interest comprising one of a binding pair, a polymer of interest and a reporter molecule can be configured into a number of different assay formats, wherein one, two, three, four or more targets can be monitored simultaneously. Such simultaneous assays can be conducted using one or more devices that carry the conjugates on a suitable solid phase, as described herein and as known in the art, such as plastic, such as a microtiter plate, or a membrane, such as nitrocellulose, glass fiber, polyethylene, other bibulous or non-bibulous paper and so on. A single device can contain a plurality of conjugates to detect a plurality of targets. Such a multiplex device can detect two, three, four or more targets.

Once the above assay configuration is incorporated, it can be seen that the number of molecules or markers detected can be single or plural in an assay or on a device. Thus, a chip microarray can also be constructed. Using the same principle, a high-density microarray can also be developed for the simultaneous identification of multiple targets including proteins, toxins, viruses, bacteria, bacterial spores, drugs, chemical agents, pollutants and/or any other target of interest. The resulting microarrays can be constructed using a lateral flow assay format. Another assay format is a plate microarray and/or a bead array, as offered by BD, Illumina and Luminex, or a combination thereof.

Such assays can be configured to contain a plurality of biomarkers that are diagnostic for a desired purpose. Thus, such a multiplex device, which can be a nanoarray or microarray, can be diagnostic for a pathologic state, reveal reaction to stimulus, such as a food or drug, and so on. The number of biomarkers used will depend on the endpoint and generally will be the minimal number of markers needed to demonstrate whether the endpoint exists. Thus, as known in the art, determining exposure of a host to a pathogen can rely on a single diagnostic antibody that binds said pathogen. Reactivity to a drug may require a larger number of biomarkers as the impact of a drug on a host may trigger reaction in a number of cellular functions. Moreover, the biomarkers used may need to be optimized to operate on a majority of a randomly breeding population or a plurality of assays may be required using different sets of biomarkers in each assay. The biomarkers detected can be any target molecule for valid binders or a binder, should the target molecule have plural, and perhaps many, copies of the epitope, determinant, ligand, binding partner and the like for binding to the capture binding partner as well as the detector binding partner with which the reporter does interact, are available. Thus, any of the known diagnostic antigens now detected for diagnostic purposes can be a target molecule for use in an assay of interest, such as cancer antigens, such as PSA and CEA, albumin, tissue proteins, such as those with are diagnostic of state of health or disease, such as proteins indicative of cardiac damage, thyroid function and the like, troponins, myoglobin, BNP's, myeloperoxidase, microbes, including viruses, such as hepatitis viruses, influenza viruses, herpes viruses and HPV, and bacteria, such as chlamydia, staphylococci and streptococci, hormones, such as hCG, estrogens, progestins, peptide hormones, such as FSH and LH, and androgens, CKMB, pharmaceuticals, such as barbiturates, anti-HIV drugs, cocaine, THC, amphetamines, morphine and other opiates, biologics, such as interferons, cytokines and the like for detecting infection, a circulating antibody generated to a non-self or self antigen, and so on. The target can be protein, carbohydrate or lipid, for example, but generally is a molecule in solution when used in a lateral flow format. Thus, suitable samples which can be added directly to the device of interest include body fluids, such as blood, serum, saliva, urine, tears, vaginal secretions, semen, tissue extracts and the like. The sample can be diluted as needed, using a suitable diluent. In other formats of assay using a reagent of interest, the target can be a cell, a tissue sample, an organ sample and other larger entities not necessarily amenable to a flow format.

The preferred conjugates of the present invention include those where a modified branched polymer conjugate comprises at least one modified branched polymer associated with at least one unit of at least one biologically active material or biological response indicator. The polymer of interest can include those that do not contain a core or those that contain a core and asymmetrical or symmetrical branches, such as those disclosed in Tomalia's polyamidoamine dendrimers such as those disclosed in U.S. Pat. Nos. 4,435,548; 4,507,466; 4,568,737; 4,587,329; 5,338,532; 5,527,524; 5,714,166, polyethyleneimine dendrimers such as those disclosed in U.S. Pat. Nos. 4,631,337, polypropyleneimine dendrimers such as those disclosed in 5,530,092; 5,610,268; 5,698,662, dendrigafts such as those disclosed in Tomalia's U.S. Pat. No. 5,773,527 and Yin's U.S. Pat. Nos. 5,631,329 and 5,919,442, as well as random asymmetrically branched polyethyleneimine and regular asymmetrically branched polylysine.

As taught hereinabove, the surfaces to which the modified branched polymer conjugate may be bound are varied and may include glass, nitrocellulose, paper, quartz, plastic, metal, colloidal particles including colloidal gold, colloidal silver and colloidal platinum, polymer or latex beads, inorganic particles, silicon wafers, colored latex particles, particles containing fluorescent or colored materials, clay, ceramic, silicon-based or ceramic semiconductor particles, silicon or ceramic semiconductor chips, nanocrystals, quantum dots, and up-converting phosphorescent particles. Quantum dots are inorganic nanoparticles (often less than 5 inn in diameter) capable of emitting different colors of light by controlling the composition and size of the material contained within the particle. Up-converting phosphors are submicron ceramic microparticles that emit visible light on excitation with near-infrared light. Such particles have sizes ranging from 100 nm to 500 nm and comprise rare earth ions, e.g., ytterbium, which are capable of absorbing two photons of infrared light. Due to the absence of autofluorescence in the background, these microparticles are often utilized as a tagging moiety for biological assays.

The reagents enable a number of different assay designs and the assays showed a number of advantages over the traditional lateral flow assays. First, the conjugates of interest in an assay allow rapid replacement of various detector antibodies without the need for colloidal gold conjugation. The traditional lateral flow assay requires the detector moiety (i.e., an antibody) to be directly linked with the label moiety, the current embodiments do not. The current approach significantly decreases the assay development time and production costs. Second, the assay design allows the control spot(s) to be located anywhere in the detection area, while the control line in the traditional lateral flow assays is always located after the test line. Third, due to the density of microarray design enabled by the conjugates of interest, many targets can be detected simultaneously on a single strip. FIG. 7 illustrates an imago of a positive microarray test with the capability to detect multiple targets simultaneously. Fourth, an internal positive control or standard can be readily introduced into the array of interest so that more accurate and quantitative observations can be achieved. Fifth, due to the high density of spots on a single strip, an accurate visual detection, particularly with the unaided eye is no longer possible. The instant assays are amenable to interfacing with an optical reader having automated spot location and quantification software. The reader can not only minimize subjectivity and human error during detection, but more importantly provide quantitative results, along with data storage and data management capabilities which have never been achieved in the traditional lateral flow assay art. Those capabilities are key requirements for the near patient care/diagnostics of the future.

Figure 11:
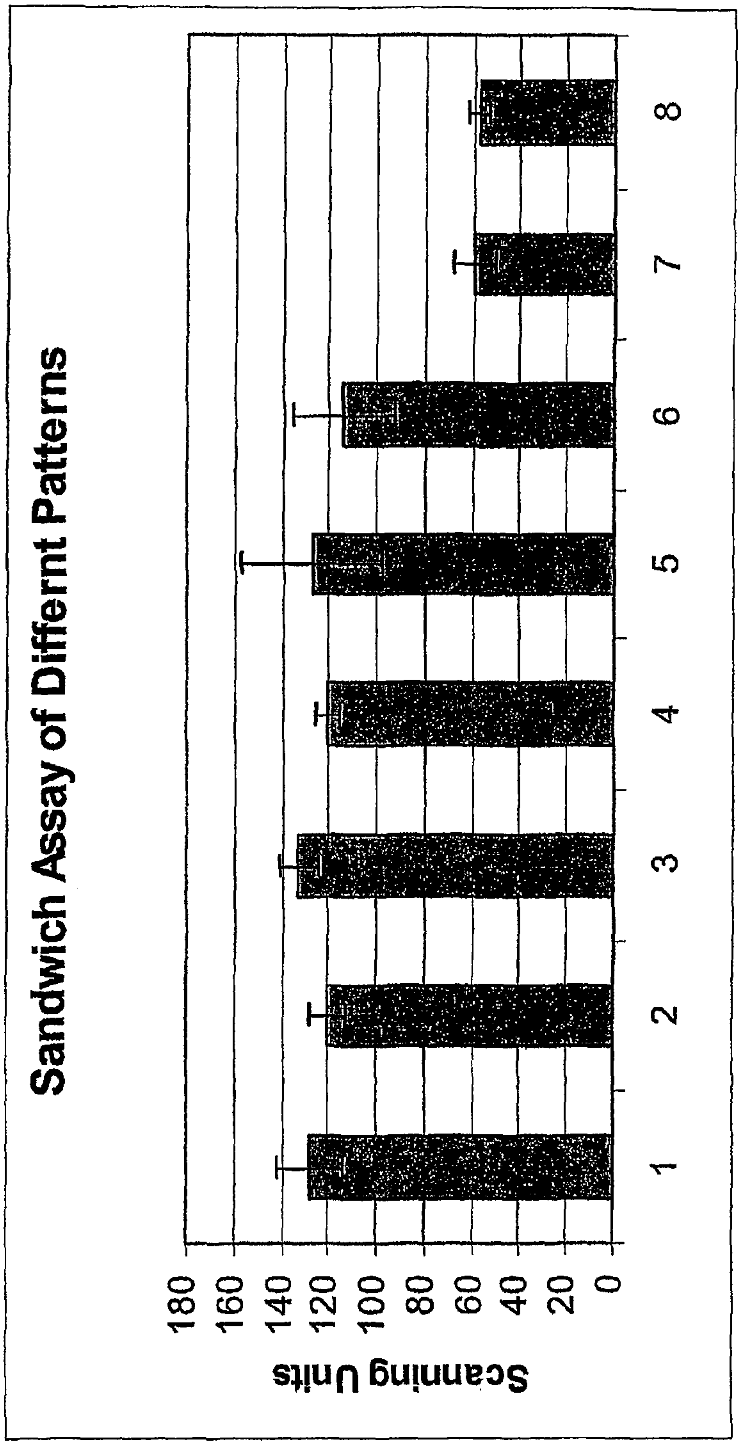
FIG. 11 presents a comparison of testing results between sandwich immunoassays with colloidal gold and detector antibody incorporated separately vs. those combined together, using the assay formats provided in FIG. 5. MSBP is mixed symmetric branched polymer. MABP is mixed asymmetric branched polymer.

In addition to the above advantages, the MBP based lateral flow assays have also shown significantly improved sensitivity over the traditional lateral flow assays. FIG. 9 illustrates a comparison test between non-polymer and polymer based lateral flow sandwich assays, while FIG. 10 illustrates a comparison between non-polymer and polymer based lateral flow direct immunoassays. In both sandwich and direct immunoassay formats, MBP-based assays are much more sensitive than non-MBP-based assays. Even when directly comparing polymer based sandwich assays, for example, one which involves the direct linking of a detector antibody to colloidal gold (FIG. 11, samples (7) and (8)) with assays that do not use a detector antibody that is directly labeled (FIG. 11, samples (1-6)), significantly enhanced sensitivity was seen in the latter assays.

Finally, due to the simple, yet flexible assay design of interest, one can substitute antibodies with, for example, receptor, ligand or nucleic acid moieties so that the same assay format can also be used for the detection of nucleic acids, carbohydrates and any ligand from an unknown sample.

The above assay strip can be placed in any plastic case or device as known to the skill of the art, and such assay kits can be readily used for field or home detection/diagnostic related applications. The total weight of this strip or ticket can be about 4.5 g, and the dimensions can be about 2 cm (width)×7 cm (length)×0.5 cm (thickness). The casing will contain and support the strip. The casing will have a means for introducing the liquid sample and a means for visualizing the result of the assay. The casing also will contain various membranes, absorbent pads, voids and the like to capture and retain liquids introduced into the casing.

Once the sample solution, including but not limited to, environmental samples such as water samples, potential pollutants and the like; and medical samples such as whole blood, plasma, serum, urine and tissue; is applied on the adsorbent pad through either a sample well or applied using a dipstick, the sample carrying the target or ligand of interest will move rapidly along the membrane and be captured by, for example, the capture antibody (in a sandwich assay format), followed by reaction with, for example, a biotinylated detector antibody, and subsequently, in the ease of biotin, a streptavidin gold conjugate, to show color change (positive test). In the absence of antigen, no color will appear in the test zone, since no immunocomplex can be formed. The time required for detection is about 15 minutes.

The assay can be configured to be qualitative, that is, the results will be presented in a form and manner that yields in a robust fashion either a positive or a negative result for what the assay is intended to provide with results visually discernable.

On the other hand, the assay format is amenable to yielding quantifiable results. Thus, the ticket can be scanned by a device that provides a measure for the level of reaction. Also, the assay can be associated with a form of calibration, either internal, external or both.

For external calibration, one approach, as known in the art, is to use serial dilutions of reagents to obtain a graded level of reaction depending on the amount of reactant present. The relationship can be used to develop a "standard curve" or a mathematical formula describing the relationship between amount and reaction level. The reaction level of an "unknown" sample can be use to extrapolate an amount of target present in the sample using the mathematical correlation or standard curve. Other means of external calibration are known and can be employed as a design choice.

For internal calibration, a known reactant, generally unrelated to the target of interest and one which will not generate a cross reaction, can be applied to the solid phase. The reactant can be one that is recognized by the existing labeling reagents on the solid phase or the solid phase can be supplemented to include additional reagent(s) that will react with the internal calibration reactant to yield a detectable signal. The amounts of the internal calibration reagents are adjusted to ensure a consistent signal, independent of the target, from assay to assay. Other means of internal calibration are known and can be employed as a design choice.

According to the same assay design, a microarray-based assays can be constructed in a similar manner. In this case, for example, capture antibodies are spotted on a solid surface through commercially available microarray robots. Detector antibodies can be mixed together. On the addition of an unknown sample in a direct, indirect, or sequential sandwich assay format, positive tests show red color changes in the corresponding capture antibody locations predetermined on the surface, while the negative tests exhibit no color changes. Alternatively, in a competition assay format, the reverse is true. Again, the polymer of interest can be utilized to affix the antibodies or antigens to the solid surface.

The instant invention contemplates kits comprising storable, shelf-stable reagents that comprise an assay, such as those described hereinabove. Shelf stability can be gauged by storage time at room temperature, at refrigerator temperatures and so. The kits can comprise a plurality of vials comprising liquid reagents or desiccated reagents to be reconstituted with an appropriate diluent, such as sterile water or a buffer. The kit can comprise a device housing the various reagents, such as a known pregnancy test kit, a lateral flow immunoassay kit and so on. Thus, the assay format for the kit can be in the form or shape of a dipstick, a wand, a slide and the like. Generally such devices comprise a plastic holder with appropriate solid phases, such as a plastic, a membrane, a paper and the like.

When such kits are configured, and when practicing an assay using an MBP of interest, the various reagents of the assay can be placed onto a solid surface, a surface of a device, a surface of a kit and so on, and stored in preparation of use. As used herein, "bound" as used in the context of attachment of a molecule to a solid phase indicates that the molecule is affixed to the surface in a permanent fashion. Thus, the molecule can be covalently bound to the solid phase. That is in distinction from "reversibly bound" which is meant to indicate that a molecule can be placed onto the solid phase at particular sites for storage purposes, such as, spotting a reagent onto a solid phase and allowing the mixture to dry or be desiccated in situ. However, when the sample, generally in a liquid form, is applied to the solid phase, as well as any other liquid phase, when the liquid contacts the molecule that is reversibly bound, that reversibly found molecule is mobilized from the solid phase and joins the liquid phase, that is, is suspended in the liquid phase.

The results of the assays of the instant invention can be ascertained by a mechanical means. The mechanical means can be any physical device that senses or detects the particular physical characteristics of the reporter molecule or a product of the reporter molecule. The mechanical device can be one that is situated in a laboratory setting, or may be situated in a movable setting for point of use applications, such as a hand held device. The device can be made into smaller, portable formats for more directed point of use applications, such as in a hospital room, physician's office, in the field and the like. Examples of portable devices and hand-held devices that can be used to detect spectrophotometric, luminescent, chemiluminescent, fluorescent or colorimetric reporter molecules are provided, for example, in U.S. Pat. Nos. 5,083,868; H1563; 6,480,115; 6,394,952; 5,900,379; 6,663,833; 6,656,745; 6,267,722; 6,706,539; 5,646,735; 6,346,984; 6,002,488; 5,962,838; 4,917,495; 6,575,368; and 6,583,880.

Such a mechanical device is one that has a detecting or sensing means for ascertaining, particularly the reporter molecule. A detecting means is one that is suitable for determining the presence of a particular reporter molecule. A radioactive reporter molecule is detectable with, for example, a scintillation counter or a Geiger-Muller counter. A light-emitting, fluorescent or luminescent reporter molecule is detectable with, for example, a colorimeter, a refractometer, a reflectometer, a photosensing device comprising, for example, a photomultiplier tube, a scanner, a charge coupled device (CCD) image sensor, a complementary metal oxide semiconductor (CMOS) image sensor and the like.

The device also can comprise a data processing means whereby the detected signal is processed and digitized. The processing means often is termed a central processing unit, a CPU, or a microprocessor, such as a semiconductor chip where data processing and analysis occurs. The digitized information either is stored in a self-contained data storage device, such as a tape, diskette, hard drive and the like or is communicated via data communication means, such as wired computer communication means or by wireless means using appropriate means, such as infrared, radiowave, microwave and the like, to a remote data storage means or a data processing means wherein the information is analyzed.

The device can contain a data input means. For example, the device can include a keyboard, a scanner and the like to provide commands for implementation by the device or to associate identifying information with data. The scanner can be one that obtains and stores an image, or can be one that interprets a code, such as a bar code, see for example, U.S. Pat. Nos. 5,885,530 and 6,099,469.

Thus, the remote detecting device can contain data processing means, such as a circuit board having an integrated circuit thereon, see for example, U.S. Pat. Nos. 5,494,798 and 6,480,115, with software to control operation of the device. The remote device can comprise a data storage means, which may be removable, such as a diskette, "stick" and other data storage forms. If not removable, the stored data can be accessible via a data communication means. Such communication means can be a hard wire for direct download of data, or such communication can take an alternative form as known in the art, such as wireless signal, for example, shortwave signals, such as radio frequencies, microwaves and infrared. Such wireless signals can be transmitted via antennae or by satellite.

For example, the information can be analyzed to compare experimental and control runs. Alternatively, the experimental run, either as a raw figure or as a figure corrected by the control is compared to population mean values. The data reduction and analyzing can be accomplished using any of a variety of available algorithms or which can be developed to yield software means for obtaining the appropriate analysis of data and to obtain a suitable output of results.

The device can contain a display means, such as a CRT or liquid crystal display, wherein the detected and/or analyzed data is appropriately processed, for example, compared with control data relating to previously obtained population data, and the data is provided to the device operator. The data can be presented as desired, for example as provided hereinabove, the raw data, relative data once adjusted for control values, or both, can be displayed on the remote device, see for example, U.S. Pat. No. 5,885,530 for point of use results.

Alternatively, the digitized information can be communicated to a data storage means, the data storage means being contained within the device or separate from the device. The digitized information can be communicated to the external storage means using known communication means. The data contained in the storage means then can be communicated with a CPU for appropriate data analysis.

Examples of such devices with data processing interfaces and means include U.S. Pat. Nos. 5,543,920; 5,589,932; and 6,362,886.

In another embodiment of this invention, asymmetrically branched polymers can be utilized to carry bioactive materials for both in vitro and in vivo related applications. The bioactive materials comprise a variety of molecules, particularly those with the ability to bind another molecule, such as a biological polymer, such as a polypeptide, a polynucleotide, a lipid, a polysaccharide, an enzyme, a receptor, an antibody, a vitamin, a lectin and so on. The target may be a pathogen, such as a parasite, a bacterium, a virus, or a toxin, such as venom. The bioactive materials can be used for a variety of uses, including as a diagnostic agent, a therapeutic agent and so on. By "diagnostic agent" is meant a molecule which can be used as a marker for a particular disease, physiological state or stage, a pathological stage or state, and so on. Albumin, mineral level, microorganism, specific antibody, specific antigen, toxin and so on are examples of diagnostic agents. Therapeutic agents are those that confer a beneficial effect, such as a drug, a nutrient, a protein and so on. It is not uncommon for a particular target to be both a diagnostic agent and a therapeutic agent.

Due to the ability to produce unevenly distributed pocket sizes and various functional groups either in the interior or at the exterior, these asymmetrically branched polymers, on proper modification, are capable of carrying a variety of materials ranging from small molecules, such as metal ions and drugs, to other large bioactive materials, such as proteins and DNA.

A polymer of interest may be used to encapsulate a bioactive bioactive molecule, particularly pharmaceuticals.

The "microcapsule" can be made as taught herein and as known in the art. The conjugate of interest also can be contained within a microcapsule or capsule, see, for example, Microencapsulation, Methods and Industrial Applications, Benita, ed., Dekker, 1996. The microcapsules can be made in a dry state mixture or reaction, or can be made in a liquid state mixture or reaction.

Microcapsules can be administered to a host in a variety of ways including oral, IM, SC, IV, rectal, topical and so on, as known in the art.

The instant microcapsules can be used in topical applications, such as creams, ointments, lotions, unguents, other cosmetics and the like. Pharmaceuticals and other bioactive or inert compounds can be encapsulated such as emollients, bleaching agents, antiperspirants, pharmaceuticals, moisturizers, scents, colorants, pigments, dyes, antioxidants, oils, fatty acids, lipids, inorganic salts, organic molecules, opacifiers, vitamins, pharmaceuticals, keratolytic agents, UV blocking agents, tanning accelerators, depigmenting agents, deodorants, perfumes, insect repellants and the like.

Drugs that can be carried by a polymer of interest include, but are not limited to, anesthetics, antibiotics, antifungals, antivirals, analgesics, antihypertensives, antiinflammatories, antidotes, antihistamines, chemotherapeutic agents, hormones, antidepressants, depressants, stimulants, tranquilizers, urinary antiinfectives, vasoconstrictors, vitamins, cardioactive drugs, immunosuppressives, nutritional supplements, and the like. Specific examples are lidocaine, bupivacaine, hydrocortisone, chlorpheniramine, triprolidine, dextromethorphan, codeine, methidizine, trimeprizine, atropine, 2-PAM chloride, homatropine, levodopa, cyclizine, meclizine, scopolamine, acetaminophen, amphotericin B, amphetamine, methatnphetamine, dextroamphetamine, propanolol, procainamide, disopyraminide, quinidine, encamide, milrinone, amrinone, dobutamine, enalapril, colnidine, hydralazine, guanadrel, ciprofloxacin, norfloxacin, tetracycline, erythromycin and quinolone drugs.

Large bioactive materials that can be carried by a polymer of interest may include, but are not limited to, proteins, recombinant proteins, antibodies, Fab antibody fragments, other antibody fragments that bind antigen, enzymes, DNA, recombinant DNA, DNA fragments, RNA, RNAi, recombinant RNA, RNA fragments, nucleotides, viruses, virus fragments and so on.

A conjugate of interest can be incorporated into pharmaceutical compositions suitable for administration, for example for diagnostic imaging. Such compositions typically comprise the active ingredient and a pharmaceutically acceptable carrier. As used herein, the language "pharmaceutically acceptable carrier" is intended to include any and all solvents, dispersion media, coatings, antibacterial and antifungal agents, isotonic and absorption delaying agents and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds also can be incorporated into the compositions.

A pharmaceutical composition of the invention for use as disclosed herein is formulated to be compatible with the intended route of administration. Examples of routes of administration include parenteral, e.g., intravenous, intradermal, subcutaneous, oral (e.g., inhalation), transdermal (topical), transmucosal and rectal administration, Solutions or suspensions used for parenteral, intradermal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. pH can be adjusted with acids or bases, such as HCl or NaOH. The parenteral preparation can be enclosed in ampoules, disposable syringes or multiple dose vials made of glass or plastic. Generally, an in vivo diagnostic agent will be administered orally, rectally, intravenously, intraperitoneally and so on.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bactoriostatic water, Cremophor EL® (BASF; Parsippany, N.J.) or phosphate-buffered saline (PBS). In all cases, the composition must be sterile and should be fluid to the extent that easy syringability exists. The composition must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol and the like) and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of the active ingredient plus any additional desired ingredient from a previously sterile-filtered solution thereof.

Oral compositions generally include an inert diluent or an edible carrier. The composition can be enclosed in gelatin capsules or compressed into tablets. For the purpose of oral therapeutic administration, the active compound can be incorporated with excipients and used in the form of tablets, troches or capsules. Oral compositions also can be prepared using a fluid carrier to yield a syrup or liquid formulation, or for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compound is delivered in the form of, for example, an aerosol spray from a pressurized container or dispenser that contains a suitable propellant, e.g., a gas such as carbon dioxide or a nebulizer, or a mist.

Systemic administration also can be by transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art.

The compound also can be prepared in the form of suppositories (e.g., with conventional suppository bases such as cocoa butter and other glycerides) or retention enemas for rectal delivery.

In one embodiment, the active compound is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid.

Methods for preparation of such formulations will be apparent to those skilled in the art. The materials also can be obtained commercially from Alza Corporation and Nova Pharmaceuticals, Inc.

Liposomal suspensions (including liposomes targeted to infected cells with monoclonal antibodies) also can be used as pharmaceutically acceptable carriers. Those can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The dosages, for example, preferred route of administration and amounts, are obtainable based on empirical data obtained from preclinical and clinical studies, practicing methods known in the art. For repeated administrations over several days or longer, depending on the condition, the treatment is sustained until a desired suppression of disease symptoms occurs. However, other dosage regimens may be useful. The progress of the therapy is monitored easily by conventional techniques and assays. An exemplary dosing regimen is disclosed in WO 94/04188. The specification for the dosage unit forms of the invention is dictated by and directly dependent on the unique characteristics of the active compound and the particular therapeutic effect to be achieved and the limitations inherent in the art of compounding such an active compound for the treatment of individuals.

The pharmaceutical compositions can be included in a container, pack or dispenser together with instructions for administration.

Another method of administration comprises the addition of a compound of interest into or with a food or drink, as a food supplement or additive, or as a dosage form taken on a prophylactic basis, similar to a vitamin. The peptide of interest can be encapsulated into forms that will survive passage through the gastric environment. Such forms are commonly known as enteric-coated formulations. Alternatively, the peptide of interest can be modified to enhance half-life, such as chemical modification of the peptide bonds, to ensure stability for oral administration, as known in the art.

The invention now will be exemplified in the following non-limiting examples.

EXAMPLES

Materials

Symmetrically branched polypropyleneimine dendrimers were purchased from Sigma-Aldrich. Symmetrically branched polyethyleneimine dendrimers and dendrigrafts were prepared according to procedures provided in U.S. Pat. Nos. 4,631,337, 5,773,527, 5,631,329, and 5,919,442. Colloidal gold particles were prepared according to procedures published in the literature (G. Frens et al., Nature Physical Science, Vol. 241, Jan. 1, 1973, 20). All of the antibodies were purchased from Sivria-Aldrich, Biodesign, or Fitzgerald.

Synthesis of Modified Symmetrically Branched PPIs with Amino Functional Groups (m-SB-PPI-$NH_2$-1.0)

The following reagents including symmetrically branched polypropyleneimine (SB-PPI-4, 8, 16, 32, 64, MW 316, 773, 1687, 3514 and 7,168), methyl acrylate (MA, FW 86.09), propylenediamine (EDA, FW=60.10) and methanol were utilized in this synthesis.

To a round bottom flask were added 1.0 g PPI-64 dendrimer (MW 7168) and 20 ml methanol (solution A). To a separate round bottom flask were added 2.4 g methylacrylate (MA) and 10 ml methanol (solution B), Solution A was then slowly dropped into solution B while stirring at room temperature. The resulting solution was allowed to react at 40° C. for 2 hours. On completion of the reaction, the solvent and unreacted MA monomer were removed by rotary evaporation, and the product, 2.5 g MA-functionalized PPI, was then redissolved in 20 ml of methanol.

To a round bottom flask were added 160 g EDA and 50 ml of methanol, followed by a slow addition of MA-functionalized PPI at 0° C. The solution was then allowed to react at 4° C. for 48 hours. The solvent and the excess EDA were removed by rotary evaporation. The crude product was then precipitated out from an ethyl ether solution, and further purified by dialysis to give about 2.8 g of primary amine-functionalized symmetrically branched PPI (m-SB-PPI-$NH_2$-1.0) with a molecular weight of about 21,760. The product was characterized by $^1H$ and $^{13}C$ nuclear magnetic resonance (NMR), and size exclusion chromatography (SEC).

Other MA or primary amine-modified symmetrically branched PPI dendrimers and symmetrically branched PEI dendrigrafts with various molecular weights were prepared in a similar manner.

Synthesis of Modified Symmetrically Branched PM with Mixed Hydroxyl and Amino Functional Groups (mix-m-SB-PPI-64-$NH_2$/OH-2)

The following reagents including amino-functionalized symmetrically branched polypropyleneimine (m-SB-PPI-64-$NH_2$-1.0), MA, EDA, monoethanolamine (MBA, FW=61.08), and methanol were utilized in this synthesis.

To a round bottom flask were added 1.0 g amino-modified PPI or m-SB-PPI-$NH_2$-1.0 produced from the previous procedure and 20 ml of methanol (solution A). To a separate round bottom flask were added 2.4 g of MA and 10 ml methanol (solution B). Solution A was then slowly dropped into solution B while stirring at room temperature. The resulting solution was allowed to react at 40° C. for 2 hours. On completion of the reaction, the solvent and unreacted monomer MA were removed by rotary evaporation, and the product, 2.5 g MA-functionalized m-SB-PPI-64-MA-1.5, was then redissolved in 20 ml of methanol.

To a round bottom flask were added 32 g EDA, 130 g MEA and 100 ml methanol (the mole ratio of EDA:MEA is 20:80), followed by slow addition of m-SB-PPI-64-MA-1.5 at 0° C. The solution was then allowed to react at 4° C. for 48 hours. The solvent and the excess EDA were removed by rotary evaporation. The crude product was then precipitated from an ethyl ether solution, and further purified by dialysis to give about 2.8 g of mixed hydroxyl and amino-functionalized (mix surface) SBP (mix-m-SB-PPI-64-$NH_2$/OH-2.0, with an average of 20% $NH_2$ and 80% OH groups and the molecular weight is about 21,862).

Other modified random AB-PEI and regular AB polylysine polymers with various ratios of hydroxyl and amino groups, as well as different molecular weights were prepared in a similar manner.

Random asymmetrically branched polyethyleneimines were purchased from Aldrich and Polysciences. Regular asymmetrically branched polymers were prepared according to procedures provided in U.S. Pat. No. 4,289,872. Colloidal gold particles were prepared according to procedures published in the literature (G. Frens et al., Nature Physical Science, Vol. 241, Jan., 1, 1973, 20). All of the antibodies were purchased from Sigma-Aldrich, Biodesign or Fitzgerald.

Synthesis of Modified Random Asymmetrically Branched PEIs with Amino Functional Groups (m-ran-AB-PEI-$NH_2$-1.0)

The following reagents including random asymmetrically branched polyethyleneimine (ran-AB-PEI, MW 2,000, 25,000, and 75,000), methyl acrylate (MA, FW=86.09), ethylenediamine (EDA, FW=60,10) and methanol were utilized in this synthesis.

To a round bottom flask were added 1.0 g PEI (MW 2,000) and 20 ml methanol (solution A). To a separate round bottom flask were added 3.0 g methylacrylate (MA) and 10 ml methanol (solution B). Solution A was then slowly dropped into solution B while stirring at room temperature. The resulting solution was allowed to react at 40° C. for 2 hours. On completion of the reaction, the solvent and unreacted MA monomer were removed by rotary evaporation, and the product, MA-functionalized PEI, was then redissolved in 20 ml of methanol.

To a round bottom flask were added 80 g EDA and 50 ml of methanol, followed by a slow addition of MA-functionalized PM at 0° C. (1 g MA dissolved in 20 ml methanol). The solution was then allowed to react at 4° C. for 48 hours. The solvent and the excess EDA were removed by rotary evaporation. The crude product was then precipitated out from an ethyl ether solution, and further purified by dialysis to give about 3.0 g of primary amine-functionalized random asymmetrically branched PEI (m-ran-AB-PEI-$NH_2$-1.0) with a molecular weight of about 7300. The product was characterized by $^1H$ and $^{13}C$ nuclear magnetic resonance (NMR), and size exclusion chromatography (SEC).

Other MA or primary amine-modified random asymmetrically branched PEI and regular asymmetrically branched polylysine polymers with various molecular weights were prepared in a similar manner.

Synthesis of Modified Random Asymmetrically Branched PEIs with Mixed Hydroxyl and Amino Functional Groups (m-ran-AB-PEI-$NH_2$/OH-2)

The following reagents including amino-functionalized random asymmetrically branched polyethyleneimine (m-ran-AB-PEI-$NH_2$-1.0), MA, EDA, monoethanolamine (MEA, FW=61.04 and methanol were utilized in this synthesis.

To a round bottom flask were added 1.0 g amino-modified PEI or m-ran-AB-PET-$NH_2$-1.0 produced from the previous procedure and 20 ml of methanol (solution A). To a separate round bottom flask were added 3.0 g of MA and 10 ml methanol (solution B). Solution A was then slowly dropped into solution B while stirring at room temperature. The resulting solution was allowed to react at 40° C. for 2 hours. On completion of the reaction, the solvent and unreacted monomer MA were removed by rotary evaporation, and the product, MA-functionalized m-ran-AB-PEI-MA-1.5, was then redissolved in 20 ml of methanol.

To a round bottom flask were added 60 g EDA, 244 g MBA and 100 ml methanol (the mole ratio of EDA:MEA is 20:80), followed by slow addition of m-ran-AB-PEI-MA-1.5 at 0° C. (1 g MA dissolved in 20 ml of methanol). The solution was then allowed to react at 4° C. for 48 hours. The solvent and the excess EDA were removed by rotary evaporation. The crude product was then precipitated from an ethyl ether solution, and further purified by dialysis to give about 2.4 g of mixed hydroxyl and amino-functionalized random ABP (m-ran-AB-PEI-$NH_2$/OH-2.0, with an average of 20% $NH_2$ and 80% OH groups and the molecular weight is about 18,000).

Other modified random AB-PEI and regular AB polylysine polymers with various ratios of hydroxyl and amino groups, as well as different molecular weights were prepared in a similar manner.

Synthesis of Alkyl-Modified Random Asymmetrically Branched Poly(2-ethyloxazoline) (PEOX) with Primary Amine Chain End Group The synthesis of $CH_3$—$(CH_2)_{18}$-PEOXABP100 (ABP 100 is an arbitrary name to denote the ratio of monomer to initiator in the initial reaction) is provided as a general procedure for the preparation of core-shell nanocapsules. A mixture of $CH_3(CH_2)_{18}CH_2$—Br (3.36 g) in 500 ml of toluene was azeotroped to remove water with a distillation head under $N_2$ for about 15 min. 2-Ethyloxazoline (100 g) was added dropwise through an addition funnel, and the mixture was allowed to reflux between 24 and 48 hours. On completion of the polymerization, 12.12 g of EDA were added to the reactive polymer solution (A) to introduce the amine function group. The molar ratio of polyoxazoline chain end to EDA is 1 to 20.

Morpholine also can be added to terminate the reaction. Thus, morpholine was added to the reactive polymer solution (A) to terminate the reaction. The crude product was re-dissolved in methanol and then precipitated out from a large excess of diethyl ether. The bottom layer was re-dissolved in methanol and dried by rotary evaporation and vacuum to give an asymmetrically random core-shell hyper-branched PEOX polymer as a white solid (101 g). Other asymmetrically hyperrandom-branched polymers such as $C_6$-PEOX ABP20, 50, 100, 200, 300, 500, $C_{12}$-PEOX ABP20, 50, 200, 300, 500, $C_{22}$-PEOX ABP20, 50, 100, 200, 300, 500, and polystyrene-PEOX etc. as well as non-modified and modified poly(2-substituted oxazoline) such as poly(2-methyl oxazoline) polymers were prepared in a similar manner. All the products were analyzed by SEC and NMR.

Preparation of Mixed Surface Modified Symmetrical Branched Polymer-IgG Conjugates The preparation of mixed surface (OH/$NH_2$ mix) modified symmetrically branched polypropyleneimine IgG conjugates (mix-m-SB-PPI-64-$NH_2$/OH-2 IgG conjugates) is provided as a general procedure for the preparation of polymer-antibody and polymer-streptavidin conjugates. Other conjugates such as m-SB-PPI-4-$NH_2$-1-IgG, m-SB-PPI-8-$NH_2$-1-IgG, m-SB-PPI-16-$NH_2$-1-IgG, m-SB-PPI-32-$NH_2$-1-IgG, m-SB-PPI-4-$NH_2$-2-IgG, m-SB-PPI-8-$NH_2$-2-IgG, m-SB-PPI-16-$NH_2$-2-IgG, m-SB-PPI-4-$NH_2$-3-IgG, m-SB-PPI-8-$NH_2$-3-IgG, m-SB-PPI-16-$NH_2$-3-IgG, m-SB-PPI-32-$NH_2$-3-IgG, and mix-m-SB-PPI-4-$NH_2$/OH-1 (OH/$NH_2$ mix)-IgG, mix-m-SB-PPI-8-$NH_2$/OH-1 (OH/$NH_2$ mix)-IgG, mix-m-SB-PPI-16-$NH_2$/OH-1 (OH/$NH_2$ mix)-IgG, mix-m-SB-PPI-32-$NH_2$/OH-1 (OH/$NH_2$ mix)-IgG, mix-m-SB-PPI-4-$NH_2$/OH-2 (OH/$NH_2$ mix)-IgG, mix-m-SB-PPI-8-$NH_2$/OH-2 (OH/$NH_2$ mix)-IgG, mix-m-SB-PPI-16-$NH_2$/OH-2 (OH/$NH_2$ mix)-IgG, mix-m-SB-PPI-32-$NH_2$/OH-2 (OH/$NH_2$ mix)-IgG, mix-m-SB-PPI-4-$NH_2$/OH-3 (OH/$NH_2$ mix)-IgG, mix-m-SB-PPI-8-$NH_2$/OH-3 (OH/$NH_2$ mix)-IgG, mix-m-SB-PPI-16-$NH_2$/OH-3 (OH/$NH_2$ mix)-IgG, mix-m-SB-PPI-32-$NH_2$/OH-3 (OH/$NH_2$ mix)-IgG, as well as primary amine and mix OH/$NH_2$ modified Combburst PEI dendrigrafts (Generation 0-5) are also conducted in a similar manner. The synthesis of other protein with modified symmetrically branched polymers is also conducted in a similar manner. The biotinylated-IgG conjugates were synthesized as provided in Bioconjugate Techniques (G. Hermanson, Academic Press, 1996).

LC-SPDP-mixed surface m-SB-PPI-64-$NH_2$/OH-2

To the mixed surface randomly branched mix-m-SB-PPI-64-$NH_2$/OH-2 ($4\times10^{-7}$ mol) in 400 μl of phosphate buffer (20 mM phosphate and 0.1 M NaCl, pH 7.5) were added $4.0\times10^{6}$ mol of sulfo-LC-SPDP (Pierce, Ill.) in 400 μl of water. This was vortexed and incubated at 30° C. for 30 minutes. The LC-SPDP-mix-m-SB-PPI-64-$NH_2$/OH-2 was purified by gel filtration chromatography and equilibrated with buffer A (0.1 M phosphate, 0.1 M NaCl and 5 mM EDTA, pH 6.8). It was further concentrated to yield 465 μl of solution, with a concentration of approximately 0.77 nmol.

Thiolated mix m-SB-PH-64-$NH_2$/OH-2 from LC-SPDP mix-m-SB-PPI-64-$NH_2$/OH-2:

The LC-SPDP mix-m-SB-PPI-64-$NH_2$/OH-2 (50 nmol in 65 μl of buffer A) was mixed with 100 μl of dithiothreitol (DTT) (50 mM in buffer A) and was incubated at room temperature for 15 minutes. Excess DTT and byproducts were removed by gel filtration with buffer A. It was concentrated in a 10 K Centricon Concentrator to yield 390 μl of the thiolated mix-m-SB-PPI-64-$NH_2$/OH-2 that was used for conjugation with the activated antibody.

Maleimide R (MAL-R)-activated Antibody:

To the antibody in PBS (310 μL, 5.1 mg or 34 nmol) were added 20.4 μl of a MAL-R-NHS (N-hydroxysuccinimide) solution (10 mM in water). The mixture was vortexed and incubated at 30° C. for 15 minutes. It was purified by gel filtration with buffer A. The maleimide-R-activated antibody was used for conjugation with the thiolated mix-m-SB-PPI-64-$NH_2$/OH-2.

mix-m-SB-PPI-64-$NH_2$/OH-2-Antibody Conjugate:

To the thiolated mix-m-SB-PPI-64-$NH_2$/OH-2 (310 μl or 35.7 nmol) was added the MAL-R-activated antibody (4.8 mL or 34 nmol). The reaction mixture was concentrated to approximately 800 μl, which was allowed to incubate overnight at 4° C., or at room temperature for about 1 hr. On completion, the reaction was quenched with 100 μL of ethyl maleimide (50 mmolar solution), and the conjugate was then fractionated on a carboxymethyl cellulose column (5 ml) with a sodium chloride step gradient in 20 mM phosphate buffer at pH 6. The conjugate was eluted with a sodium chloride gradient, and characterized by cationic exchange chromatography, UV spectroscopy, and polyacrylamide gel electrophoresis.

Conjugation via Reductive Coupling

Reduction of Antibody:

To the antibody, 2.1 mg or 14 nmol in 160 μL of buffer B (containing 0.1 M sodium phosphate, 5 mM EDTA, and 0.1 M NaCl, pH 6.0) were added 40 μL of DTT (50 mM in buffer B). The solution was allowed to stand at room temperature for 30 min. It was purified by gel filtration in a Sephadex G-25 column equilibrated with buffer B. The reduced antibody was concentrated to 220 μL, and was used for the following conjugation.

MAL-R-Mixed Surface Modified SBP:

To the mixed surface modified SBP in 400 μL ($400\times10^{-9}$ mols) at pH 7.4 were added 400 μL of MAL-R-NHS (10 mM in water). This was mixed and incubated at 30° C. for 15 mm. On termination, it was purified on a Sephadex G-25 column equilibrated with buffer B. The MAL-R-mixed surface modified SBP was collected and stored in aliquots in the same buffer at −40° C.

Mixed surface Modified SBP-Antibody Conjugate:

To the reduced antibody (14 nmols in 220 μL) was added the MAL-R-mix-m-SB-PPI-64-$NH_2$/OH-2 (154 μL, 16.6 nmols) with stirring. To this were added 12.5 μL of sodium carbonate (1.0 M solution) to bring the pH to 6.8. The reaction was continued for 1 hr at room temperature. It was terminated with the addition of 100 μL of cysteamine (0.4 mM solution). The conjugation mixture was purified on a CM cellulose column with a sodium chloride gradient elution.

Preparation of IgG-Asymmetrical Randomly Branched Polymer Conjugates

The preparation of randomly branched mixed surface (OH/$NH_2$ mix) m-ran-AB-PEI-$NH_2$/OH-2 IgG conjugates is provided as a general procedure for the preparation of polymer-antibody and polymer-streptavidin conjugates. Other conjugates such as PEI-IgG, m-ran-AB-PEI-$NH_2$-1-IgG, m-ran-AB-PEI-$NH_2$-2-IgG, m-ran-AB-PEI-$NH_2$-3-IgG, m-ran-AB-PEI-$NH_2$-4-IgG, as well as m-ran-AB-PEI-$NH_2$/OH-1 (OH$NH_2$ mix)-IgG, m-ran-AB-PEI-$NH_2$/OH-2 (OH/$NH_2$ mix)-IgG, m-ran-AB-PEI-$NH_2$/OH-3 (OH/$NH_2$ mix)-IgG, regular polylysine polymer, alkyl-modified random branched poly(2-ethyloxazoline) with primary amine chain ends were all synthesized in a similar manner. The synthesis of various protein conjugates with asymmetrically random branched PEOX polymers is also conducted in a similar manner. The biotinylated-IgG conjugates were synthesized as provided in Bioconjugate Techniques (G. Hermanson, Academic Press, 1996).

LC-SPDP-mixed surface m-ran-AB-PEI-$NH_2$/OH-2:

To the mixed surface randomly branched m-ran-AB-PEI-$NH_2$/OH-2 ($4\times10^{-7}$ mol) in 400 μl of phosphate buffer (20 mM phosphate and 0.1 M NaCl, pH 7.5) were added $4.0\times10^{-6}$ mol of sulfo-LC-SPDP (Pierce, Ill.) in 400 μl of water. This was vortexed and incubated at 30° C. for 30 minutes. The LC-SPDP-m-ran-AB-PEI-$NH_2$/OH-2 was purified by gel filtration chromatography and equilibrated with buffer A (0.1 M phosphate, 0.1 M NaCl and 5 mM EDTA, pH 6.8). It was further concentrated to yield 465 μl of solution, with a concentration of approximately 0.77 nmol/μmol.

Thiolated rn-ran-AB-PEI-$NH_2$/OH-2 from LC-SPDP m-an-AB-PEI-$NH_2$/OH-2:

The LC-SPDP m-ran-AB-PEI-$NH_2$/OH-2 (50 nmol in 65 ml of buffer A) was mixed with 100 μl of dithiothreitol (DTT) (50 mM in buffer A) and was allowed to incubate at room temperature for 15 minutes. Excess DTT and byproducts were removed by gel filtration with buffer A. It was concentrated in a 10 K Centricon Concentrator to yield 390 μl of the thiolated m-ran-AB-PEI-$NH_2$/OH-2 that was used for conjugation with the activated antibody.

Maleimide-R-activated antibody made as described above was used for conjugation with the thiolated m-ran-AB-PEI-$NH_2$/OH-2.

m-ran-AB-PEI-$NH_2$/OH-2-Antibody Conjugate:

To the thiolated m-ran-AB-PEI-$NH_2$/OH-2 (310 μl or 35.7 nmol) was added the MAL-R-activated antibody (4.8 ml, or 34 nmol). The reaction mixture was concentrated to approximately 800 μl, which was allowed to incubate overnight at 4° C., and at room temperature for about 1 hr. On completion, the reaction was quenched with 100 μL of ethyl maleimide (50 mmolar solution), and the conjugate was then fractionated on a carboxymethyl cellulose column (5 ml) with a sodium chloride step gradient in 20 mM phosphate buffer at pH 6. The conjugate was eluted with a sodium chloride gradient, and characterized by cationic exchange chromatography, UV spectroscopy, and polyacrylamide gel electrophoresis.

Colloidal Gold-Based Immunoassays

Preparation of Gold-Ab Conjugates;

To a 125 ml flask were added 60 ml of colloidal gold solution (20-80 nm in diameter as measured by TEM, O.D. 1.078 as measured by IN spectroscopy) (Frens et al., supra). The pH of the solution was adjusted to 8-11 by addition of a 0.2 M potassium carbonate solution. To this solution were added 600 μl of conjugated antibody solution (0.1). 0.1-1.5 in sodium borate buffer) while stirring, followed by subsequent addition of 600 μl of bovine serum albumin (20% with sodium azide stabilizer). The mixture was stirred at 20° C. for 20-240 more minutes. The solution remained purple in color and some foaminess was observed. On completion, the stir bar was removed, and the reaction mixture was transferred to two 50 ml conical tubes. The material was centrifuged until very little color was observed in the supernatant. The supernatant was removed and 600 μl of 25 mM sodium borate buffer were added in each tube. The contents were mixed thoroughly and the two tubes of material were combined and characterized by UV-Vis.

The gold-modified branched polymer (MBP)-streptavidin conjugates were prepared in a similar manner. The gold-MBP-streptavidin-biotin-Ab conjugates were prepared through subsequent addition of biotinylated Ab to gold-SBP-streptavidin conjugates. Standard antibody biotinylation protocols can be found for example, in Bioconjugate Techniques (G. T. Hermanson, Academic Press, 1996). Other biologically active molecules, which can be used as reporters, such as horseradish peroxidase (HRP) or avidin and derivatives and analogs thereof can also be attached to gold in a similar manner. However, during the test, additional substrates have to be added to achieve signal enhancement.

Lateral Flow or Dipstick Immunoassay Ticket Experiments

An immunoassay device or “ticket” can consist of a strip of cellulose or other membrane in a membrane-retaining device, generally composed of an inert plastic, an adsorbent pad and a receiving pad at the ends of the membrane.

Figure 5:
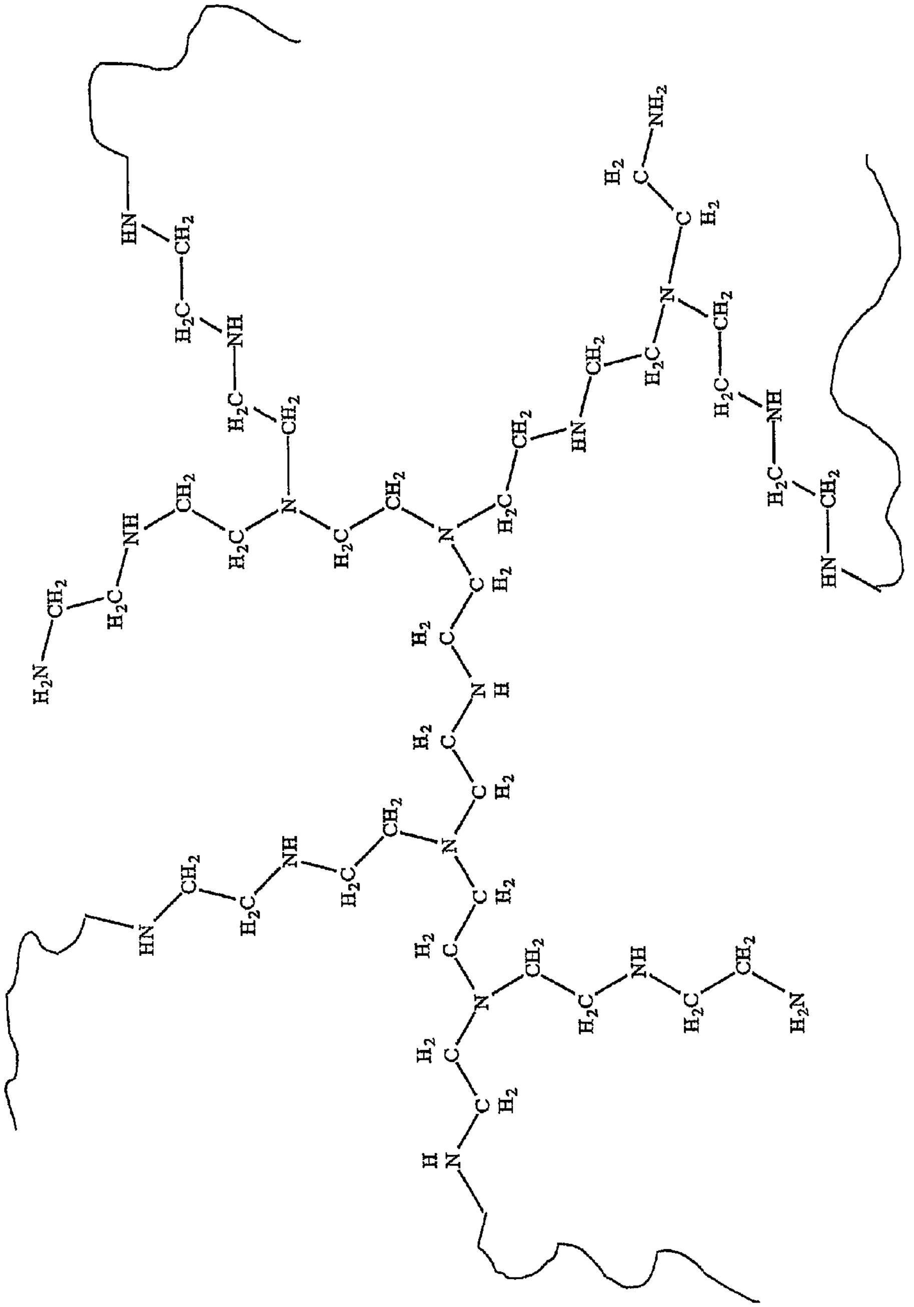
FIG. 5 depicts the chemical structure of a random asymmetrically branched polyethyleneimine polymer.
Figure 6:
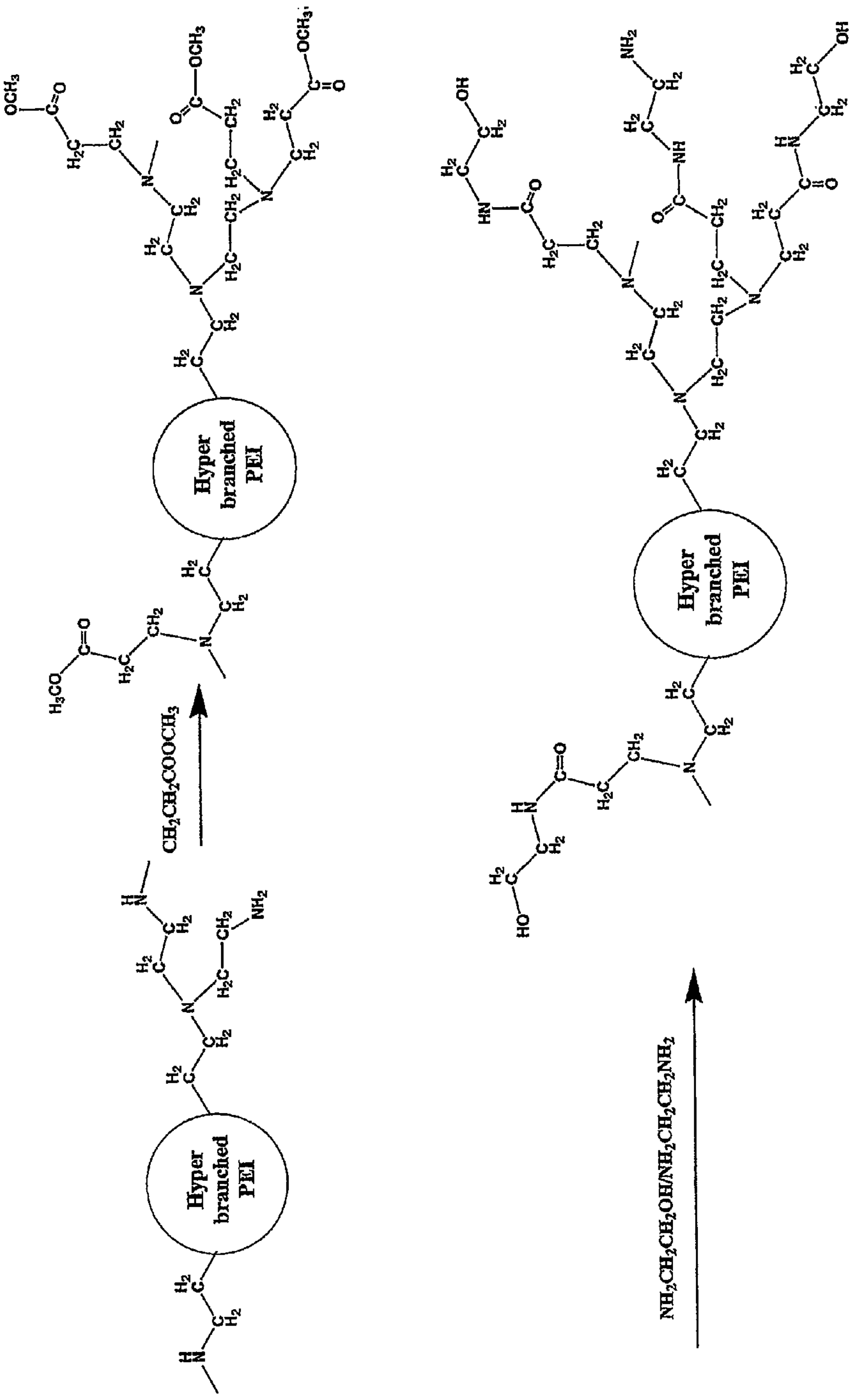
FIG. 6 depicts chemical modification reactions of random asymmetrically branched polyethyleneimine polymers.

FIG. 8 illustrates a number of lateral flow-based immunoassay configurations. For example, FIG. 8A represents the configuration of an immunoassay ticket without a plastic cover: a) absorbent pad, b) biotinylated Ab, either on a separate pad or on the adsorbent pad, c) streptavidin-gold conjugate, d-g) capture Abs for different targets, h) control Ab and i) liquid receiving pad. FIG. 8B represents the configuration of an immunoassay ticket without a plastic cover: a) absorbent pad, b) streptavidin-gold conjugate, either on a separate pad or on the adsorbent pad, c) biotinylated Ab, d-g) capture Abs for different targets, h) control Ab and i) liquid receiving pad. FIG. 8C represents the configuration of an immunoassay ticket without a plastic cover: a) absorbent pad, b) streptavidin-gold conjugate, either on a separate pad or on the absorbent pad, c) biotinylated Ab, (b and c are on top of each other), d-g) capture Abs for different targets, h) control Ab and i) liquid receiving pad. FIG. 8D represents the configuration of an immunoassay ticket without a plastic cover: a) absorbent pad, b) biotinylated Ab, either on a separate pad or on the absorbent pad, c) streptavidin-gold conjugate, (b and c are on top of each other), d-g) capture Abs for different targets, h) control Ab and i) liquid receiving pad. FIG. 8E represents the configuration of an immunoassay ticket without a plastic cover: a) absorbent pad, b) biotinylated Ab, streptavidin-gold conjugate, (a, b, c are on the same pad), d-g) capture Abs for different targets, h) control Ab and i) liquid receiving pad. FIG. 5F represents the configuration of an immunoassay ticket without a plastic cover: a) absorbent pad, b) streptavidin-gold conjugate, c) biotinylated Ab, (a, b, c are on the same pad), d-g) capture Abs for different targets, h) control Ab and i) liquid receiving pad. FIG. 8G represents the configuration of an immunoassay ticket without a plastic cover: a) absorbent pad, b) biotinylated Ab, c) streptavidin-gold conjugate, d-g) capture Abs for different targets, h) control Ab and i) liquid receiving pad. a-h) are on the same membrane. FIG. 8H represents configuration of an immunoassay ticket without a plastic cover: a) absorbent pad, b) streptavidin-gold conjugate, c) biotinylated Ab, d-g) capture Abs for different targets, h) control Ab and i) liquid receiving pad. a-h) are on the same membrane. The dipstick assays work in a similar manner.

A number of different assays of varying formats were constructed and tested amongst similar such assays containing a conjugate of interest and also with assays not containing a conjugate of interest, for example, having a directly labeled detector molecule.

The assays containing a conjugate of interest were superior.

It will be apparent to one skilled in the art that various changes, alterations, and modifications of the present invention are possible in light of the above teachings. It is therefore to be understood that while the invention has been described in this specification with some particularity, it is not intended to limit the invention to the particular embodiments provided herein. On the contrary, it is intended to cover all alternatives, modifications, and equivalents as may be included within the spirit and scope of the invention.

All references cited herein are herein incorporated by reference in entirety.

The invention claimed is:

1. An assay kit for detecting, an antibody in a sample, comprising: a) a detector that specifically binds said antibody of said sample, said detector tagged with a plurality of a first member of a first binding pair; b) a conjugate comprising a modified dendritic polymer and a second member of said first binding pair; (c) a capture molecule comprising a molecule which is specifically bound by said antibody in said sample; and (d) a reporter.

2. The kit of claim 1, wherein said first binding pair comprises an antibody, an antigen binding portion thereon an antigen, an epitope-containing portion thereof, a nucleic acid, a nucleic, acid binding moiety, a lectin, a cognate saccharide thereof, a ligand, a hapten, a hormone, a hormone receptor, an enzyme, an enzyme cofactor, an enzyme substrate, a biotin or a molecule that binds biotin.

3. The kit of claim 1, wherein said reporter comprises a colored, luminescent or fluorescent particulate or moiety, an enzyme, or a combination thereof.

4. The kit of claim 3, wherein said fluorescent or luminescent particulate or moiety comprises quantum dots, nanocrystals, up-converting phosphorescent particles or fluorophore containing latex beads.

5. The kit of claim 3, wherein said colored particulate comprises colloidal metals, comprising gold or silver, colored latex beads or colored dyes.

6. The kit of claim 1, wherein said conjugate (b) and said reporter (c) are joined.

7. The kit of claim 1, wherein said kit comprises a solid phase comprising said capture molecule, said detector, said conjugate and said reporter.

8. The kit of claim 7, wherein said solid phase comprises a flat surface or a membrane.

9. The kit of claim 8, wherein said flat surface comprises a silicon wafer, quartz, glass, a metal, or a plastic.

10. The kit of claim 8, wherein said membrane comprises a paper, a plastic membrane, a nylon membrane or a nitrocellulose membrane.

11. The kit of claim 7, wherein said solid phase comprises a microarray or a bead array.

12. The kit of claim 7, wherein said solid phase comprises a dipstick, a lateral flow immunoassay or a microarray.

13. The kit of claim 7, wherein said capture molecule is affixed directly or indirectly to said solid phase.

14. The kit of claim 7, wherein said conjugate is reversibly bound to said solid phase.

15. The kit of claim 7, wherein said solid phase comprises a microtitre plate.

16. The kit of claim 1, wherein said reporter yields a product which is detectable by color or by light.

17. The kit of claim 1, wherein said first member or said second member of said first binding pair is an antibody or antigen-binding portion thereof.

18. The kit of claim 1, wherein said first member or said second member of said first binding pair is a molecule that binds biotin, fluorescein, nucleic acid, albumin, to hapten or a combination thereof.

19. The kit of claim 1, wherein said detector is an antibody, an antigen-binding portion thereof, an antigen, an epitope-containing portion thereof, a nucleic acid or a nucleic acid binding moiety.

20. The kit of claim 1, where said first member or said second member of said first binding pair comprises biotin, fluorescein, nucleic acid, albumin, a hapten or a combination thereof.

* * * * *